(12) United States Patent
Paluszcyk et al.

(10) Patent No.: US 11,160,973 B2
(45) Date of Patent: *Nov. 2, 2021

(54) DEEP TREATMENT DRESSINGS

(71) Applicant: Vomaris Innovations, Inc., Tempe, AZ (US)

(72) Inventors: Troy Paluszcyk, Tempe, AZ (US); Michael Nagel, Tempe, AZ (US)

(73) Assignee: Vomaris Innovations, Inc., Tempe, AZ (US)

(*) Notice: Subject to any disclaimer, the term of this patent is extended or adjusted under 35 U.S.C. 154(b) by 84 days.

This patent is subject to a terminal disclaimer.

(21) Appl. No.: 16/094,357

(22) PCT Filed: Apr. 25, 2017

(86) PCT No.: PCT/US2017/029426
§ 371 (c)(1),
(2) Date: Oct. 17, 2018

(87) PCT Pub. No.: WO2017/189584
PCT Pub. Date: Nov. 2, 2017

(65) Prior Publication Data
US 2019/0117958 A1    Apr. 25, 2019

Related U.S. Application Data

(60) Provisional application No. 62/327,202, filed on Apr. 25, 2016.

(51) Int. Cl.
*A61N 1/04* (2006.01)
*A61N 1/32* (2006.01)
*A61N 1/20* (2006.01)

(52) U.S. Cl.
CPC ............. *A61N 1/0492* (2013.01); *A61N 1/04* (2013.01); *A61N 1/0428* (2013.01); *A61N 1/0468* (2013.01); *A61N 1/0476* (2013.01); *A61N 1/205* (2013.01); *A61N 1/32* (2013.01)

(58) Field of Classification Search
CPC ........ A61N 1/0492; A61N 1/205; A61N 1/32; A61N 1/04; A61N 1/0476; A61N 1/0468; A61N 1/0428
See application file for complete search history.

(56) References Cited

U.S. PATENT DOCUMENTS

| 2013/0103129 A1* | 4/2013 | Turner ................. A61N 1/0488 607/116 |
| 2016/0058999 A1* | 3/2016 | Skiba ..................... A61N 1/205 607/50 |

FOREIGN PATENT DOCUMENTS

WO    2017/189584 A1    11/2017

OTHER PUBLICATIONS

International Search Report and Written Opinion for International Application No. PCT/US2017/029426 dated Aug. 1, 2017.

* cited by examiner

*Primary Examiner* — Rex R Holmes
(74) *Attorney, Agent, or Firm* — K&L Gates LLP; Louis C. Cullman; Hal Gibson

(57) ABSTRACT

A deep treatment bioelectric device includes multiple electrodes joined with a planar substrate.

9 Claims, 4 Drawing Sheets

DEEP TREATMENT DRESSINGS

RELATED APPLICATIONS

This application is an application under 35 U.S.C. § 371 of International Patent Application PCT/US2017/029426 filed on Apr. 25, 2017, which claims the benefit of U.S. Provisional Patent Application No. 62/327,202, filed Apr. 25, 2016, the disclosures of each of which are incorporated herein by reference in their entirety.

FIELD

The present specification relates to bioelectric devices and methods of manufacture and use thereof.

BACKGROUND

Biologic tissues and cells are affected by electrical stimulus. Accordingly, devices and techniques for applying electric stimulus to tissue have been developed to address a number of medical issues. The present specification relates to systems, methods and devices useful for applying electric fields and/or currents to a treatment area.

SUMMARY

Disclosed herein are systems, devices, and methods for use in treatment of subjects, in particular deeper treatment of tissue than is possible with current practices. For example, disclosed are array and substrate configurations that can provide higher voltage and greater current values as compared to current practices, and thus provide treatment to, for example, a greater area and/or depth as measured from or at the exterior wound surface. Disclosed embodiments comprise methods for prevention of biofilms. Disclosed embodiments comprise methods for treatment of biofilms. Disclosed embodiments comprise use of disclosed devices in combination with active agents, for example, antibacterial agents.

In embodiments the systems, devices, and methods include substrates, for example dressings or fabrics, for example bandages, that comprise one or more biocompatible electrodes configured to generate at least one of a low level electric field (LLEF) or low level electric current (LLEC). Embodiments disclosed herein can produce a uniform current or field density.

In certain embodiments, the substrate comprising the one or more biocompatible electrodes can comprise one layer of a composite dressing, for example a composite wound dressing comprising the substrate, an adhesive layer, an absorbent layer that can, in embodiments, be expandable. In embodiments the adhesive layer can be stretchable or expandable to accommodate body movements.

The systems and devices can comprise corresponding or interlocking perimeter areas to assist the devices in maintaining their position on the patient and/or their position relative to each other. In certain embodiments, the systems and devices can comprise a port or ports to provide access to the interior of the device or the treatment area beneath the device.

Certain embodiments can comprise a solution or formulation comprising an active agent. Certain embodiments can comprise a solvent or carrier or vehicle.

In embodiments, the substrate can comprise a "tab" to allow the user to remove the dressing from the backing layer or card. In embodiments, the tab can be reversibly attached to both the substrate as well as the backing layer, and used to remove the substrate from the backing layer. During application of the dressing to a treatment area, the tab can be removed.

In embodiments, the backing layer covers the adhesive to maintain the adhesive's effectiveness prior to use and provide for more efficient storage. For example, an irregularly-shaped bandage can be associated via adhesive with a square or rectangular backing layer to provide a more efficiently-stored system.

DETAILED DESCRIPTION

Figure 1:
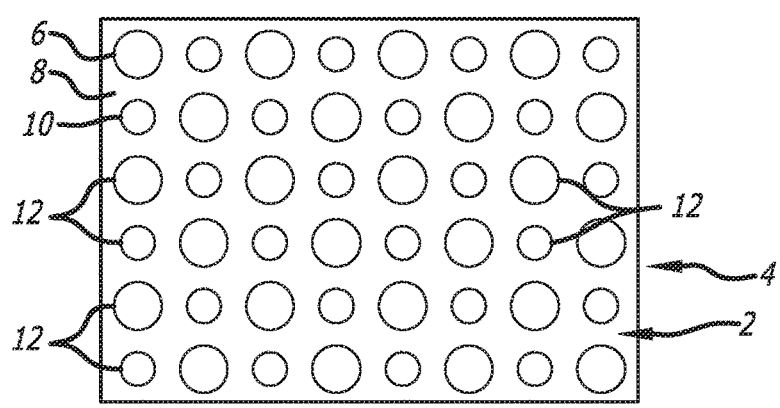
FIG. 1 depicts a detailed plan view of a substrate layer microcell pattern disclosed herein.
Figure 2:
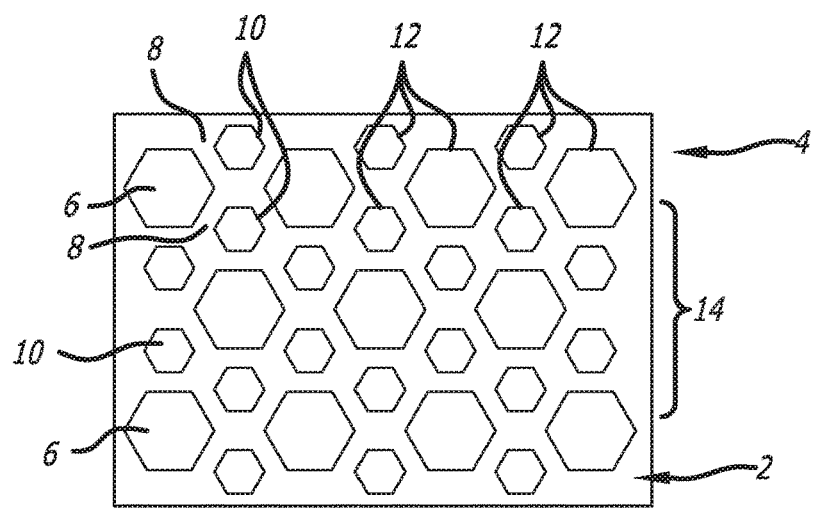
FIG. 2 depicts a detailed plan view of a substrate layer microcell pattern of applied electrical conductors according to one or more embodiments.
Figure 3:
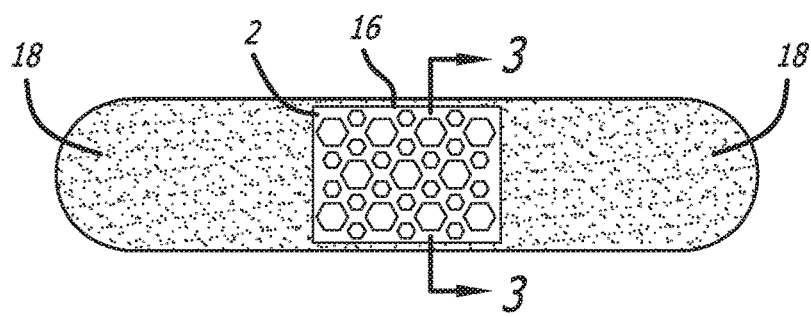
FIG. 3 depicts an embodiment using the applied pattern of FIG. 2 according to one or more embodiments.
Figure 4:
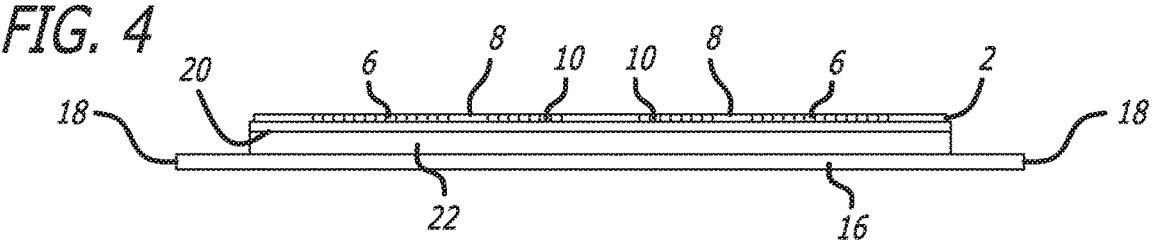
FIG. 4 depicts a cross-section of FIG. 3 through line 3-3 according to one or more embodiments.

Embodiments disclosed herein comprise methods, systems and devices that can provide a low level electric field (LLEF) to a treatment area of greater depth or area than those known in the art or, when brought into contact with an electrically conducting material, can provide a low level electric current (LLEC) to a treatment area of greater depth or area than those known in the art. In embodiments an LLEC system is an LLEF system that is in contact with an electrically conducting material, for example a liquid. In certain embodiments, the micro-current or electric field can be modulated, for example, to alter the duration, size, shape, field depth, duration, current, polarity, or voltage of the system.

Aspects disclosed herein comprise composite devices that can comprise a matrix, for example a multi-array matrix on a substrate layer, for example a planar substrate layer. Such matrices can include a first electrode or a first array comprising a pattern of microcells formed from a first conductive solution, the first solution comprising a metal species; and a second electrode or a second array comprising a pattern of microcells formed from a second conductive solution, the second solution comprising a metal species capable of defining at least one voltaic cell for spontaneously generating at least one electrical current with the metal species of the first electrode or array when said first and second electrodes or arrays are introduced to an electrolytic solution and said first and second electrodes or arrays are not in physical contact with each other. Certain embodiments can utilize an external power source such as AC or DC power or pulsed RF or pulsed current, such as high voltage pulsed current. In embodiments, the electrical energy is derived from the dissimilar metals creating a battery at each cell/cell interface, whereas those embodiments with an external power source can require conductive electrodes in a spaced apart configuration to predetermine the electric field shape and strength.

Embodiments can comprise an expandable absorbent layer that can absorb excess fluid from the substrate and expand away from the treatment area, thus preventing oversaturation of the treatment area with resultant maceration and increased infection risk. In embodiments the absorbent layer cab be non-expandable.

Embodiments can comprise a stretchable, expandable film layer that can stretch to accommodate a larger volume, for example as an expandable absorbent layer absorbs liquid. This aspect can be mechanically decoupled from the adhesive layer in order to reduce shear forces on the skin. Additionally, in embodiments the vertically-expanding absorbent layer and film allows the dressing to absorb more volume of fluid in a smaller contact area ("footprint"). In embodiments the film layer can be non-expandable.

Disclosed systems, devices, and methods comprise wound dressings that can reduce or eliminate painful shear force caused by standard dressings. Certain embodiments can also allow for improved/complete articulation of a treated area for example the knee or elbow, or another contoured area of the body.

Embodiments can comprise a non-restrictive adhesive layer. Embodiments can comprise elongated areas, or "flanges" to wrap around the treatment area surrounding the treated joint.

A dressing disclosed herein and placed over tissue such as a joint can move relative to the tissue. Reducing the amount of motion between tissue and dressing can be advantages to healing. In embodiments, traction or friction blisters can be treated, minimized, or prevented. The use of the dressing as a temporary bridge to reduce stress across a treatment site can reduce stress at the sutures or staples and this will reduce scarring and encourage healing.

Definitions

"Activation agent" as used herein means a composition useful for maintaining a moist environment within and about the skin. Activation agents can be in the form of gels (for example a hydrogel) or liquids. Activation agents can be conductive. Activation agents can also be antibacterial. In one embodiment, an activation agent can be a liquid such as sweat or topical substance such as petroleum jelly (for example with a conductive component added).

"Active agent" as used herein means an ingredient or drug that is biologically active and can be present in a formulation or solution. For example, an antibiotic is an active agent—such an agent can kill or inhibit the growth of bacteria. Disclosed formulations can contain more than one active ingredient.

"Affixing" as used herein can mean contacting a patient or tissue with a device or system disclosed herein. In embodiments "affixing" can comprise the use of straps, elastic, adhesive, etc.

"Antimicrobial agent" or "antibacterial" or "antibiotic" as used herein refers to an agent that kills or inhibits the growth of microorganisms. Antibacterial agents are used to disinfect surfaces and eliminate potentially harmful bacteria. Unlike antibiotics, they are not used as medicines for humans or animals, but are found in products such as soaps, detergents, health and skincare products and household cleaners. Antibacterial agents may be divided into two groups according to their speed of action and residue production: The first group contains those that act rapidly to destroy bacteria, but quickly disappear (by evaporation or breakdown) and leave no active residue behind (referred to as non-residue-producing). Examples of this type are the alcohols, chlorine, peroxides, and aldehydes. The second group consists mostly of compounds that leave long-acting residues on the surface to be disinfected and thus have a prolonged action (referred to as residue-producing). Common examples of this group are triclosan, triclocarban, and benzalkonium chloride. Another type of antimicrobial agent can be an anti-fungal agent that can be used with the devices described herein.

"Applied" or "apply" as used herein refers to contacting a surface with a conductive material, for example printing, painting, or spraying a conductive ink on a surface. Alternatively, "applying" can mean contacting a treatment area with a device or system disclosed herein.

"Backing layer" or "card" as used herein refers to a layer with which the substrate comprising the multi-array matrix is associated, for example reversibly associated using an adhesive. A backing layer can include a port or void area of an appropriate shape, for example, a square, a circle, a slit, etc.

"Conductive material" as used herein refers to an object or type of material which permits the flow of electric charges in one or more directions. Conductive materials can comprise solids such as metals or carbon, or liquids such as conductive metal solutions and conductive gels. Conductive materials can be applied to form at least one matrix. Conductive liquids can dry, cure, or harden after application to form a solid material. Solid material can also be cast from a polymer solution that contains conductive material and water wherein the water evaporates when the conductive liquids dry, cure, or harden. Solid material can then be activated for use, for example when soaked in water.

"Cosmetic product" as used herein means substances used to enhance the appearance of the body. They are generally mixtures of chemical compounds, some being derived from natural sources, many being synthetic. These products are generally liquids or creams or ointments intended to be applied to the human body for maintaining, cleansing, beautifying, promoting attractiveness, or altering the appearance. These products can be electrically conductive.

"Discontinuous region" as used herein refers to a "void" in a material such as a hole, slit, slot, or the like. The term can mean any void in the material though typically the void is of a regular shape. A void in the material can be enclosed entirely within the perimeter of a material or it can extend to the perimeter of a material.

"Dots" as used herein refers to discrete deposits of similar or dissimilar reservoirs that can, in certain embodiments, function as at least one battery cell. The term can refer to a deposit of any suitable size or shape or conductive material, such as squares, circles, triangles, lines, etc.

"Electrode" refers to similar or dissimilar conductive materials. In embodiments utilizing an external power source the electrodes can comprise similar conductive materials. In embodiments that do not use an external power source, the electrodes can comprise dissimilar conductive materials that can define an anode and a cathode.

"Expandable" as used herein refers to the ability to stretch while retaining structural integrity and not tearing. The term can refer to solid regions as well as discontinuous or void regions; solid regions as well as void regions can stretch or expand. "Expandable" can refer to stretching along any axis, including the "Z" axis, that is, wherein the dressing expands away from the treatment site while maintaining contact with the treatment site.

"Interlocking" as used herein refers to areas on the perimeter of disclosed devices that complement other areas on the perimeter such that the areas engage with each other by the fitting together of projections and recesses. This design can enable disclosed devices to "nest" closely together to treat multiple areas in close proximity to one another.

"Matrix" or "matrices" as used herein refer to an electrode or pattern or patterns, such as those formed by electrodes on a substrate, such as a fabric or a fiber or microparticle, or the like. Matrices can also comprise a pattern or patterns within a solid or liquid material or a three dimensional object. Matrices can be designed to vary the electric field or electric current or microcurrent generated. For example, the strength and shape of the field or current or microcurrent can be altered, or the matrices can be designed to produce an electric field(s) or current or microcurrent of a desired strength or shape.

"Reduction-oxidation reaction" or "redox reaction" as used herein refers to a reaction involving the transfer of one or more electrons from a reducing agent to an oxidizing agent. The term "reducing agent" can be defined in some embodiments as a reactant in a redox reaction, which donates electrons to a reduced species. A "reducing agent" is thereby oxidized in the reaction. The term "oxidizing agent" can be defined in some embodiments as a reactant in a redox reaction, which accepts electrons from the oxidized species. An "oxidizing agent" is thereby reduced in the reaction. In various embodiments a redox reaction produced between a first and second reservoir provides a current between the dissimilar reservoirs. The redox reactions can occur spontaneously when a conductive material is brought in proximity to first and second dissimilar reservoirs such that the conductive material provides a medium for electrical communication and/or ionic communication between the first and second dissimilar reservoirs. In other words, in an embodiment electrical currents can be produced between first and second dissimilar reservoirs without the use of an external battery or other power source (e.g., a direct current (DC) such as a battery or an alternating current (AC) power source such as a typical electric outlet). Accordingly, in various embodiments a system is provided which is "electrically self contained," and yet the system can be activated to produce electrical currents. The term "electrically self contained" can be defined in some embodiments as being capable of producing electricity (e.g., producing current) without an external battery or power source. The term "activated" can be defined in some embodiments to refer to the production of electric current through the application of a radio signal of a given frequency or through ultrasound or through electromagnetic induction.

"Stretchable" as used herein refers to the ability of embodiments that stretch without losing their structural integrity. That is, embodiments can stretch to accommodate irregular skin surfaces or surfaces wherein one portion of the surface can move relative to another portion.

"Tab" as used herein refers to an area of the dressing or backing layer or substrate that provides the user means to remove the substrate from the backing layer. The tab can comprise a "tear-away" such that it is removable.

Systems, Devices, and Methods of Manufacture

Embodiments disclosed herein can comprise a substrate and one, two, or more electrodes.

Embodiments disclosed herein can comprise multiple layers. For example, an embodiment can comprise a substrate layer comprising a multi-array matrix; an adhesive layer; and an absorbent foam layer. Embodiments can be ETO, E-Beam, and Gamma Sterilization compatible.

In embodiments, disclosed methods, systems, and devices can comprise a backing layer or card with which the substrate comprising the multi-array matrix is associated. The substrate can be reversibly associated with the backing layer via, for example, an adhesive layer. The backing layer or card can comprise a void region or port. In embodiments the port can expose the multi-array matrix. This port can provide access to the multi-array matrix, for example to hydrate the matrix, to apply an active agent to the matrix, to apply a hydrogel to the matrix, or the like.

In embodiments, the backing layer or card can be shaped to follow the outline of the dressing or substrate. For example, in embodiments the backing layer or card can be circular when used with round dressings. Alternatively, the backing layer or card can comprise a shape contrasting with that of the dressing or substrate. For example, in embodiments the backing layer or card can be square or rectangular when used with round dressings. In embodiments, the system is provided as a single card associated with a single substrate or dressing. In further embodiments, the system is provided as a single card associated with multiple substrates or dressings.

The adhesive layer can, in embodiments, allow the substrate to be reversibly associated with an area where treatment is desired, for example a tissue, or the like. The adhesive layer can maintain the association between the substrate and the backing layer prior to application of the substrate to a treatment area, for example during storage periods.

The backing layer or substrate can comprise at least one "tab" to allow the user to remove the dressing comprising the substrate from the backing layer or card.

In embodiments, systems and devices disclosed herein comprise a substrate layer as shown in FIG. 1 comprising patterns of electrodes or micro-batteries that create an electric field between each dot pair. In embodiments, the field is very short, e.g. in the range of physiologic electric fields. In embodiments the field is of greater strength, for example beyond the range of physiologic electric fields. In embodiments, the direction of the electric field produced by devices disclosed herein is omnidirectional within a three dimensional material.

Figure 9:
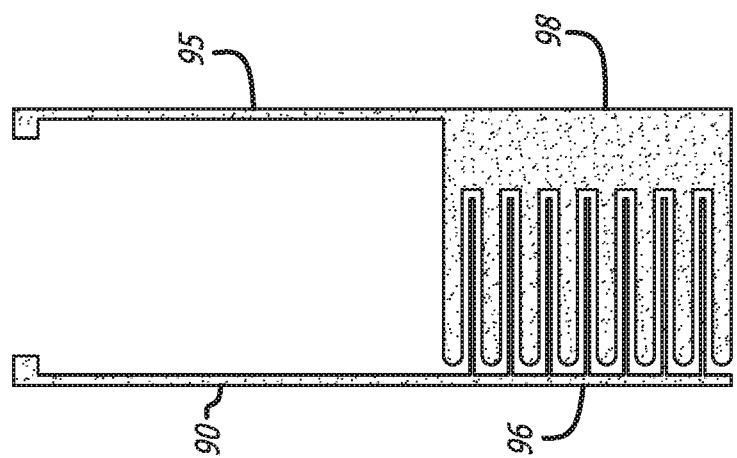
FIG. 9 depicts a detailed plan view of a substrate layer electrode pattern as disclosed herein.
Figure 8:
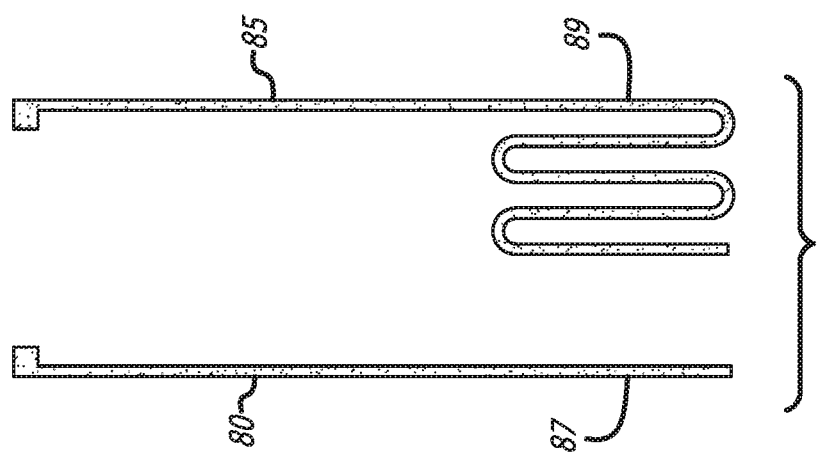
FIG. 8 depicts a detailed plan view of a substrate layer electrode pattern disclosed herein.

In embodiments, systems and devices disclosed herein comprise a substrate layer as shown in FIGS. 8-9, each substrate comprising 2 electrodes or micro-batteries that create an electric field between them. In embodiments, the field is greater than the range of physiologic electric fields. In embodiments, the direction of the electric field produced by devices disclosed herein is omnidirectional within a three dimensional material.

Substrate layers as disclosed herein can comprise absorbent or non-absorbent textiles, low-adhesives, vapor permeable films, hydrocolloids, hydrogels, alginates, foams, foam-based materials, cellulose-based materials comprising Kettenbach fibers, hollow tubes, fibrous materials, such as those impregnated with anhydrous/hygroscopic materials, beads and the like, or any suitable material as known in the art.

In embodiments, the substrate layer can comprise electrodes or microcells. Each electrode or microcell can be or comprise a conductive metal. In embodiments, the electrodes or microcells can comprise any electrically-conductive material, for example, a hydrogel, an electrically conductive hydrogel, metals, electrolytes, superconductors, semiconductors, plasmas, and nonmetallic conductors such as graphite and conductive polymers. Electrically conductive metals can comprise silver, copper, gold, aluminum, molybdenum, zinc, lithium, tungsten, brass, carbon, nickel, iron, palladium, platinum, tin, bronze, carbon steel, lead, titanium, stainless steel, mercury, Fe/Cr alloys, and the like. The electrodes can be solid, coated or plated with a different metal such as aluminum, gold, platinum or silver.

In certain embodiments, reservoir or electrode geometry can comprise circles, polygons, lines, zigzags, ovals, stars, or any suitable variety of shapes. This provides the ability to design/customize surface electric field shapes as well as depth of penetration. For example. In embodiments it can be desirable to employ an electric field of greater strength or depth in an area where, for example, skin is thicker, or where a deeper infection is present, to achieve optimal treatment. In another embodiment, the desirable strength of an electric field be employed within a three dimensional material such as a hydrogel or solid object.

Reservoir or electrode or dot sizes and concentrations can vary, as these variations can allow for changes in the properties of the electric field created by embodiments of the invention. Certain embodiments provide an electric field at about, for example, 0.5-5.0 V at the device surface under normal tissue loads with resistance of 100 ohms to 100 K ohms.

In other embodiments, a system can be provided which comprises an external battery or power source. For example, an AC power source can be of any wave form, such as a sine wave, a triangular wave, or a square wave. AC power can also be of any frequency such as for example 50 Hz or 60 HZ, or the like. AC power can also be of any voltage, such as for example 120 volts, or 220 volts, or the like. In embodiments an AC power source can be electronically modified, such as for example having the voltage reduced, prior to use.

In embodiments, systems and devices disclosed herein can apply an electric field, an electric current, or both, wherein the field, current, or both can be of varying size, strength, density, shape, or duration in different areas of the embodiment. In embodiments, systems and devices disclosed herein can apply an electric field, an electric current, or both, wherein the field, current, or both can be of uniform size, strength, density, shape, or duration. In embodiments, by micro-sizing the electrodes or reservoirs, the shapes of the electric field, electric current, or both can be customized, increasing or decreasing very localized watt densities and allowing for the design of patterns of electrodes or reservoirs wherein the amount of electric field over a tissue can be designed or produced or adjusted based upon feedback from the tissue or upon an algorithm within sensors operably connected to the embodiment and a control module. The electric field, electric current, or both can be stronger in one zone and weaker in another. The electric field, electric current, or both can change with time and be modulated based on treatment goals or feedback from the tissue or patient. The control module can monitor and adjust the size, strength, density, shape, or duration of electric field or electric current based on material parameters or tissue parameters. For example, embodiments disclosed herein can produce and maintain localized electrical events. For example, embodiments disclosed herein can produce specific values for the electric field duration, electric field size, electric field shape, field depth, current, polarity, and/or voltage of the device or system.

In various embodiments the difference of the standard potentials of the electrodes or dots or reservoirs can be in a range from about 0.05 V to approximately about 5.0 V. For example, the standard potential can be about 0.05 V, about 0.06 V, about 0.07 V, about 0.08 V, about 0.09 V, about 0.1 V, about 0.2 V, about 0.3 V, about 0.4 V, about 0.5 V, about 0.6 V, about 0.7 V, about 0.8 V, about 0.9 V, about 1.0 V, about 1.1 V, about 1.2 V, about 1.3 V, about 1.4 V, about 1.5 V, about 1.6 V, about 1.7 V, about 1.8 V, about 1.9 V, about 2.0 V, about 2.1 V, about 2.2 V, about 2.3 V, about 2.4 V, about 2.5 V, about 2.6 V, about 2.7 V, about 2.8 V, about 2.9 V, about 3.0 V, about 3.1 V, about 3.2 V, about 3.3 V, about 3.4 V, about 3.5 V, about 3.6 V, about 3.7 V, about 3.8 V, about 3.9 V, about 4.0 V, about 4.1 V, about 4.2 V, about 4.3 V, about 4.4 V, about 4.5 V, about 4.6 V, about 4.7 V, about 4.8 V, about 4.9 V, about 5.0 V, about 5.1 V, about 5.2 V, about 5.3 V, about 5.4 V, about 5.5 V, about 5.6 V, about 5.7 V, about 5.8 V, about 5.9 V, about 6.0 V, or the like.

In embodiments, systems and devices disclosed herein can produce a low level electric current of between for example about 1 and about 200 micro-amperes, between about 10 and about 190 micro-amperes, between about 20 and about 180 micro-amperes, between about 30 and about 170 micro-amperes, between about 40 and about 160 micro-amperes, between about 50 and about 150 micro-amperes, between about 60 and about 140 micro-amperes, between about 70 and about 130 micro-amperes, between about 80 and about 120 micro-amperes, between about 90 and about 100 micro-amperes, or between 100 and 150 micro-amperes, or between 150 and 200 micro-amperes, or between 200 and 250 micro-amperes, or between 250 and 300 micro-amperes, or between 300 and 350 micro-amperes, or between 350 and 400 micro-amperes, or between 400 and 450 micro-amperes, or between 450 and 500 micro-amperes, or between 500 and 550 micro-amperes, or between 550 and 600 micro-amperes, or between 600 and 650 micro-amperes, or between 650 and 700 micro-amperes, or between 700 and 750 micro-amperes, or between 750 and 800 micro-amperes, or between 800 and 850 micro-amperes, or between 850 and 900 micro-amperes, or between 900 and 950 micro-amperes, or between 950 and 1000 micro-amperes (1 milli-amp [mA]), or between 1.0 and 1.1 mA, or between 1.1 and 1.2 mA, or between 1.2 and 1.3 mA, or between 1.3 and 1.4 mA, or between 1.4 and 1.5 mA, or between 1.5 and 1.6 mA, or between 1.6 and 1.7 mA, or between 1.7 and 1.8 mA, or between 1.8 and 1.9 mA, or between 1.9 and 2.0 mA, or between 2.0 and 2.1 mA, or between 2.1 and 2.2 mA, or between 2.2 and 2.3 mA, or between 2.3 and 2.4 mA, or between 2.4 and 2.5 mA, or between 2.5 and 2.6 mA, or between 2.6 and 2.7 mA, or between 2.7 and 2.8 mA, or between 2.8 and 2.9 mA, or between 2.9 and 3.0 mA, or between 3.0 and 3.1 mA, or between 3.1 and 3.2 mA, or between 3.2 and 3.3 mA, or between 3.3 and 3.4 mA, or between 3.4 and 3.5 mA, or between 3.5 and 3.6 mA, or between 3.6 and 3.7 mA, or between 3.7 and 3.8 mA, or between 3.8 and 3.9 mA, or between 3.9 and 4.0 mA, or between 4.0 and 4.1 mA, or between 4.1 and 4.2 mA, or between 4.2 and 4.3 mA, or between 4.3 and 4.4 mA, or between 4.4 and 4.5 mA, or between 4.5 and 5.0 mA, or between 5.0 and 5.5 mA, or between 5.5 and 6.0 mA, or between 6.0 and 6.5 mA, or between 6.5 and 7.0 mA, or between 7.5 and 8.0 mA, or between 8.0 and 8.5 mA, or between 8.5 and 9.0 mA, or between 9.0 and 9.5 mA, or between 9.5 and 10.0 mA, or between 10.0 and 10.5 mA, or between 10.5 and 11.0 mA, or between 11.0 and 11.5 mA, or between 11.5 and 12.0 mA, or between 12.0 and 12.5 mA, or between 12.5 and 13.0 mA, or between 13.0 and 13.5 mA, or between 13.5 and 14.0 mA, or between 14.0 and 14.5 mA, or between 14.5 and 15.0 mA, or the like.

In embodiments, systems and devices disclosed herein can produce a low level electric current of between for example about 1 and about 400 micro-amperes, between about 20 and about 380 micro-amperes, between about 40 and about 360 micro-amperes, between about 60 and about 340 micro-amperes, between about 80 and about 320 micro-amperes, between about 100 and about 3000 micro-amperes, between about 120 and about 280 micro-amperes, between about 140 and about 260 micro-amperes, between about 160 and about 240 micro-amperes, between about 180 and about 220 micro-amperes, or the like.

In embodiments, systems and devices disclosed herein can produce a low level electric current of between for example about 1 micro-ampere and about 1 milli-ampere, between about 50 and about 800 micro-amperes, between about 200 and about 600 micro-amperes, between about 400 and about 500 micro-amperes, or the like.

In embodiments, systems and devices disclosed herein can produce a low level electric current of about 10 micro-amperes, about 20 micro-amperes, about 30 micro-amperes, about 40 micro-amperes, about 50 micro-amperes, about 60 micro-amperes, about 70 micro-amperes, about 80 micro-amperes, about 90 micro-amperes, about 100 micro-amperes, about 110 micro-amperes, about 120 micro-amperes, about 130 micro-amperes, about 140 micro-amperes, about 150 micro-amperes, about 160 micro-amperes, about 170 micro-amperes, about 180 micro-amperes, about 190 micro-amperes, about 200 micro-amperes, about 210 micro-amperes, about 220 micro-amperes, about 240 micro-amperes, about 260 micro-amperes, about 280 micro-amperes, about 300 micro-amperes, about 320 micro-amperes, about 340 micro-amperes, about 360 micro-amperes, about 380 micro-amperes, about 400 micro-amperes, about 450 micro-amperes, about 500 micro-amperes, about 550 micro-amperes, about 600 micro-amperes, about 650 micro-amperes, about 700 micro-amperes, about 750 micro-amperes, about 800 micro-amperes, about 850 micro-amperes, about 900 micro-amperes, about 950 micro-amperes, about 1 milli-ampere (mA), about 1.1 mA, about 1.2 mA, about 1.3 mA, about 1.4 mA, about 1.5 mA, about 1.6 mA, about 1.7 mA, about 1.8 mA, about 1.9 mA, about 2.0 mA, about 2.1 mA, about 2.2 mA, about 2.3 mA, about 2.4 mA, about 2.5 mA, about 2.6 mA, about 2.7 mA, about 2.8 mA, about 2.9 mA, about 3.0 mA, about 3.1 mA, about 3.2 mA, about 3.3 mA, about 3.4 mA, about 3.5 mA, about 3.6 mA, about 3.7 mA, about 3.8 mA, about 3.9 mA, about 4.0 mA, about 4.1 mA, about 4.2 mA, about 4.3 mA, about 4.4 mA, about 4.5 mA, about 4.6 mA, about 4.7 mA, about 4.8 mA, about 4.9 mA, about 5.0 mA, about 5.1 mA, about 5.2 mA, about 5.3 mA, about 5.4 mA, about 5.5 mA, about 5.6 mA, about 5.7 mA, about 5.8 mA, about 5.9 mA, about 6.0 mA, about 6.1 mA, about 6.2 mA, about 6.3 mA, about 6.4 mA, about 6.5 mA, about 6.6 mA, about 6.7 mA, about 6.8 mA, about 6.9 mA, about 7.0 mA, about 7.1 mA, about 7.2 mA, about 7.3 mA, about 7.4 mA, about 7.5 mA, about 7.6 mA, about 7.7 mA, about 7.8 mA, about 7.9 mA, about 8.0 mA, about 8.1 mA, about 8.2 mA, about 8.3 mA, about 8.4 mA, about 8.5 mA, about 8.6 mA, about 8.7 mA, about 8.8 mA, about 8.9 mA, about 9.0 mA, about 9.1 mA, about 9.2 mA, about 9.3 mA, about 9.4 mA, about 9.5 mA, about 9.6 mA, about 9.7 mA, about 9.8 mA, about 9.9 mA, about 10.0 mA, about 10.1 mA, about 10.2 mA, about 10.3 mA, about 10.4 mA, about 10.5 mA, about 10.6 mA, about 10.7 mA, about 10.8 mA, about 10.9 mA, about 11.0 mA, about 11.1 mA, about 11.2 mA, about 11.3 mA, about 11.4 mA, about 11.5 mA, about 11.6 mA, about 11.7 mA, about 11.8 mA, about 11.9 mA, about 12.0 mA, about 12.1 mA, about 12.2 mA, about 12.3 mA, about 12.4 mA, about 12.5 mA, about 12.6 mA, about 12.7 mA, about 12.8 mA, about 12.9 mA, about 13.0 mA, about 13.1 mA, about 13.2 mA, about 13.3 mA, about 13.4 mA, about 13.5 mA, about 13.6 mA, about 13.7 mA, about 13.8 mA, about 13.9 mA, about 14.0 mA, about 14.1 mA, about 14.2 mA, about 14.3 mA, about 14.4 mA, about 14.5 mA, about 14.6 mA, about 14.7 mA, about 14.8 mA, about 14.9 mA, about 15.0 mA, about 15.1 mA, about 15.2 mA, about 15.3 mA, about 15.4 mA, about 15.5 mA, about 15.6 mA, about 15.7 mA, about 15.8 mA, or the like.

In embodiments, the disclosed systems and devices can produce a low level electric current of not more than 10 micro-amperes, or not more than about 20 micro-amperes, not more than about 30 micro-amperes, not more than about 40 micro-amperes, not more than about 50 micro-amperes, not more than about 60 micro-amperes, not more than about 70 micro-amperes, not more than about 80 micro-amperes, not more than about 90 micro-amperes, not more than about 100 micro-amperes, not more than about 110 micro-amperes, not more than about 120 micro-amperes, not more than about 130 micro-amperes, not more than about 140 micro-amperes, not more than about 150 micro-amperes, not more than about 160 micro-amperes, not more than about 170 micro-amperes, not more than about 180 micro-amperes, not more than about 190 micro-amperes, not more than about 200 micro-amperes, not more than about 210 micro-amperes, not more than about 220 micro-amperes, not more than about 230 micro-amperes, not more than about 240 micro-amperes, not more than about 250 micro-amperes, not more than about 260 micro-amperes, not more than about 270 micro-amperes, not more than about 280 micro-amperes, not more than about 290 micro-amperes, not more than about 300 micro-amperes, not more than about 310 micro-amperes, not more than about 320 micro-amperes, not more than about 340 micro-amperes, not more than about 360 micro-amperes, not more than about 380 micro-amperes, not more than about 400 micro-amperes, not more than about 420 micro-amperes, not more than about 440 micro-amperes, not more than about 460 micro-amperes, not more than about 480 micro-amperes, not more than about 500 micro-amperes, not more than about 520 micro-amperes, not more than about 540 micro-amperes, not more than about 560 micro-amperes, not more than about 580 micro-amperes, not more than about 600 micro-amperes, not more than about 620 micro-amperes, not more than about 640 micro-amperes, not more than about 660 micro-amperes, not more than about 680 micro-amperes, not more than about 700 micro-amperes, not more than about 720 micro-amperes, not more than about 740 micro-amperes, not more than about 760 micro-amperes, not more than about 780 micro-amperes, not more than about 800 micro-amperes, not more than about 820 micro-amperes, not more than about 840 micro-amperes, not more than about 860 micro-amperes, not more than about 880 micro-amperes, not more than about 900 micro-amperes, not more than about 920 micro-amperes, not more than about 940 micro-amperes, not more than about 960 micro-amperes, not more than about 980 micro-amperes, not more than about 1 milli-ampere (mA), not more than about 1.1 mA, not more than about 1.2 mA, not more than about 1.3 mA, not more than about 1.4 mA, not more than about 1.5 mA, not more than about 1.6 mA, not more than about 1.7 mA, not more than about 1.8 mA, not more than about 1.9 mA, not more than about 2.0 mA, not more than about 2.1 mA, not more than about 2.2 mA, not more than about 2.3 mA, not more than about 2.4 mA, not more than about 2.5 mA, not more than about 2.6 mA, not more than about 2.7 mA, not more than about 2.8 mA, not more than about 2.9 mA, not more than about 3.0 mA, not more than about 3.1 mA, not more than about 3.2 mA, not more than about 3.3 mA, not more than about 3.4 mA, not more than about 3.5 mA, not more than about 3.6 mA, not more than about 3.7 mA, not more than about 3.8 mA, not more than about 3.9 mA, not more than about 4.0 mA, not more than about 4.1 mA, not more than about 4.2 mA, not more than about 4.3 mA, not more than about 4.4 mA, not more than about 4.5 mA, not more than about 4.6 mA, not more than about 4.7 mA, not more than about 4.8 mA, not more than about 4.9 mA, not more than about 5.0 mA, not more than about 5.1 mA, not more than about 5.2 mA, not more than about 5.3 mA, not more than about 5.4 mA, not more than about 5.5 mA, not more than about 5.6 mA, not more than about 5.7 mA, not more than about 5.8 mA, not more than about 5.9 mA, not more than about 6.0 mA, not more than about 6.1 mA, not more than about 6.2 mA, not more than about 6.3 mA, not more than about 6.4 mA, not more than about 6.5 mA, not more than about 6.6 mA, not more than about 6.7 mA, not more than about 6.8 mA, not more than about 6.9 mA, not more than about 7.0 mA, not more than about 7.1 mA, not more than about 7.2 mA, not more than about 7.3 mA, not more than about 7.4 mA, not more than about 7.5 mA, not more than about 7.6 mA, not more than about 7.7 mA, not more than about 7.8 mA, not more than about 7.9 mA, not more than about 8.0 mA, not more than about 8.1 mA, not more than about 8.2 mA, not more than about 8.3 mA, not more than about 8.4 mA, not more than about 8.5 mA, not more than about 8.6 mA, not more than about 8.7 mA, not more than about 8.8 mA, not more than about 8.9 mA, not more than about 9.0 mA, not more than about 9.1 mA, not more than about 9.2 mA, not more than about 9.3 mA, not more than about 9.4 mA, not more than about 9.5 mA, not more than about 9.6 mA, not more than about 9.7 mA, not more than about 9.8 mA, not more than about 9.9 mA, not more than about 10.0 mA, not more than about 10.1 mA, not more than about 10.2 mA, not more than about 10.3 mA, not more than about 10.4 mA, not more than about 10.5 mA, not more than about 10.6 mA, not more than about 10.7 mA, not more than about 10.8 mA, not more than about 10.9 mA, not more than about 11.0 mA, not more than about 11.1 mA, not more than about 11.2 mA, not more than about 11.3 mA, not more than about 11.4 mA, not more than about 11.5 mA, not more than about 11.6 mA, not more than about 11.7 mA, not more than about 11.8 mA, not more than about 11.9 mA, not more than about 12.0 mA, not more than about 12.1 mA, not more than about 12.2 mA, not more than about 12.3 mA, not more than about 12.4 mA, not more than about 12.5 mA, not more than about 12.6 mA, not more than about 12.7 mA, not more than about 12.8 mA, not more than about 12.9 mA, not more than about 13.0 mA, not more than about 13.1 mA, not more than about 13.2 mA, not more than about 13.3 mA, not more than about 13.4 mA, not more than about 13.5 mA, not more than about 13.6 mA, not more than about 13.7 mA, not more than about 13.8 mA, not more than about 13.9 mA, not more than about 14.0 mA, not more than about 14.1 mA, not more than about 14.2 mA, not more than about 14.3 mA, not more than about 14.4 mA, not more than about 14.5 mA, not more than about 14.6 mA, not more than about 14.7 mA, not more than about 14.8 mA, not more than about 14.9 mA, not more than about 15.0 mA, not more than about 15.1 mA, not more than about 15.2 mA, not more than about 15.3 mA, not more than about 15.4 mA, not more than about 15.5 mA, not more than about 15.6 mA, not more than about 15.7 mA, not more than about 15.8 mA, and the like.

In embodiments, systems and devices disclosed herein can produce a low level electric current of not less than 10 micro-amperes, not less than 20 micro-amperes, not less than 30 micro-amperes, not less than 40 micro-amperes, not less than 50 micro-amperes, not less than 60 micro-amperes, not less than 70 micro-amperes, not less than 80 micro-amperes, not less than 90 micro-amperes, not less than 100 micro-amperes, not less than 110 micro-amperes, not less than 120 micro-amperes, not less than 130 micro-amperes, not less than 140 micro-amperes, not less than 150 micro-amperes, not less than 160 micro-amperes, not less than 170 micro-amperes, not less than 180 micro-amperes, not less than 190 micro-amperes, not less than 200 micro-amperes, not less than 210 micro-amperes, not less than 220 micro-amperes, not less than 230 micro-amperes, not less than 240 micro-amperes, not less than 250 micro-amperes, not less than 260 micro-amperes, not less than 270 micro-amperes, not less than 280 micro-amperes, not less than 290 micro-amperes, not less than 300 micro-amperes, not less than 310 micro-amperes, not less than 320 micro-amperes, not less than 330 micro-amperes, not less than 340 micro-amperes, not less than 350 micro-amperes, not less than 360 micro-amperes, not less than 370 micro-amperes, not less than 380 micro-amperes, not less than 390 micro-amperes, not less than 400 micro-amperes, not less than about 420 micro-amperes, not less than about 440 micro-amperes, not less than about 460 micro-amperes, not less than about 480 micro-amperes, not less than about 500 micro-amperes, not less than about 520 micro-amperes, not less than about 540 micro-amperes, not less than about 560 micro-amperes, not less than about 580 micro-amperes, not less than about 600 micro-amperes, not less than about 620 micro-amperes, not less than about 640 micro-amperes, not less than about 660 micro-amperes, not less than about 680 micro-amperes, not less than about 700 micro-amperes, not less than about 720 micro-amperes, not less than about 740 micro-amperes, not less than about 760 micro-amperes, not less than about 780 micro-amperes, not less than about 800 micro-amperes, not less than about 820 micro-amperes, not less than about 840 micro-amperes, not less than about 860 micro-amperes, not less than about 880 micro-amperes, not less than about 900 micro-amperes, not less than about 920 micro-amperes, not less than about 940 micro-amperes, not less than about 960 micro-amperes, not less than about 980 micro-amperes, not less than about 1 milli-ampere (mA), not less than about 1.1 mA, not less than about 1.2 mA, not less than about 1.3 mA, not less than about 1.4 mA, not less than about 1.5 mA, not less than about 1.6 mA, not less than about 1.7 mA, not less than about 1.8 mA, not less than about 1.9 mA, not less than about 2.0 mA, not less than about 2.1 mA, not less than about 2.2 mA, not less than about 2.3 mA, not less than about 2.4 mA, not less than about 2.5 mA, not less than about 2.6 mA, not less than about 2.7 mA, not less than about 2.8 mA, not less than about 2.9 mA, not less than about 3.0 mA, not less than about 3.1 mA, not less than about 3.2 mA, not less than about 3.3 mA, not less than about 3.4 mA, not less than about 3.5 mA, not less than about 3.6 mA, not less than about 3.7 mA, not less than about 3.8 mA, not less than about 3.9 mA, not less than about 4.0 mA, not less than about 4.1 mA, not less than about 4.2 mA, not less than about 4.3 mA, not less than about 4.4 mA, not less than about 4.5 mA, not less than about 4.6 mA, not less than about 4.7 mA, not less than about 4.8 mA, not less than about 4.9 mA, not less than about 5.0 mA, not less than about 5.1 mA, not less than about 5.2 mA, not less than about 5.3 mA, not less than about 5.4 mA, not less than about 5.5 mA, not less than about 5.6 mA, not less than about 5.7 mA, not less than about 5.8 mA, not less than about 5.9 mA, not less than about 6.0 mA, not less than about 6.1 mA, not less than about 6.2 mA, not less than about 6.3 mA, not less than about 6.4 mA, not less than about 6.5 mA, not less than about 6.6 mA, not less than about 6.7 mA, not less than about 6.8 mA, not less than about 6.9 mA, not less than about 7.0 mA, not less than about 7.1 mA, not less than about 7.2 mA, not less than about 7.3 mA, not less than about 7.4 mA, not less than about 7.5 mA, not less than about 7.6 mA, not less than about 7.7 mA, not less than about 7.8 mA, not less than about 7.9 mA, not less than about 8.0 mA, not less than about 8.1 mA, not less than about 8.2 mA, not less than about 8.3 mA, not less than about 8.4 mA, not less than about 8.5 mA, not less than about 8.6 mA, not less than about 8.7 mA, not less than about 8.8 mA, not less than about 8.9 mA, not less than about 9.0 mA, not less than about 9.1 mA, not less than about 9.2 mA, not less than about 9.3 mA, not less than about 9.4 mA, not less than about 9.5 mA, not less than about 9.6 mA, not less than about 9.7 mA, not less than about 9.8 mA, not less than about 9.9 mA, not less than about 10.0 mA, not less than about 10.1 mA, not less than about 10.2 mA, not less than about 10.3 mA, not less than about 10.4 mA, not less than about 10.5 mA, not less than about 10.6 mA, not less than about 10.7 mA, not less than about 10.8 mA, not less than about 10.9 mA, not less than about 11.0 mA, not less than about 11.1 mA, not less than about 11.2 mA, not less than about 11.3 mA, not less than about 11.4 mA, not less than about 11.5 mA, not less than about 11.6 mA, not less than about 11.7 mA, not less than about 11.8 mA, not less than about 11.9 mA, not less than about 12.0 mA, not less than about 12.1 mA, not less than about 12.2 mA, not less than about 12.3 mA, not less than about 12.4 mA, not less than about 12.5 mA, not less than about 12.6 mA, not less than about 12.7 mA, not less than about 12.8 mA, not less than about 12.9 mA, not less than about 13.0 mA, not less than about 13.1 mA, not less than about 13.2 mA, not less than about 13.3 mA, not less than about 13.4 mA, not less than about 13.5 mA, not less than about 13.6 mA, not less than about 13.7 mA, not less than about 13.8 mA, not less than about 13.9 mA, not less than about 14.0 mA, not less than about 14.1 mA, not less than about 14.2 mA, not less than about 14.3 mA, not less than about 14.4 mA, not less than about 14.5 mA, not less than about 14.6 mA, not less than about 14.7 mA, not less than about 14.8 mA, not less than about 14.9 mA, not less than about 15.0 mA, not less than about 15.1 mA, not less than about 15.2 mA, not less than about 15.3 mA, not less than about 15.4 mA, not less than about 15.5 mA, not less than about 15.6 mA, not less than about 15.7 mA, not less than about 15.8 mA, and the like.

In embodiments, disclosed devices can provide an electric field of greater than physiological strength to a depth of, at least 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or more.

In embodiments the electric field can be extended, for example through the use of a hydrogel. A hydrogel is a network of polymer chains that are hydrophilic. Hydrogels are highly absorbent natural or synthetic polymeric networks. Hydrogels can be configured to contain a high percentage of water (e.g. they can contain over 90% water). Hydrogels can possess a degree of flexibility very similar to natural tissue, due to their significant water content. A hydrogel can be configured in a variety of viscosities. Viscosity is a measurement of a fluid or material's resistance to gradual deformation by shear stress or tensile stress. In embodiments the electrical field can be extended through a semi-liquid hydrogel with a low viscosity such an ointment or a cellular culture medium. In other embodiments the electrical field can be extended through a solid hydrogel with a high viscosity such as a Petri dish, clothing, or material used to manufacture a prosthetic. In general, the hydrogel described herein may be configured to a viscosity of between about 0.5 Pa·s and about $10^{12}$ Pa·s. In embodiments the viscosity of a hydrogel can be, for example, between 0.8 and $10^{12}$ Pa·s, between 1 Pa·s and $10^6$ Pa·s, between 5 and $10^3$ Pa·s, between 10 and 100 Pa·s, between 15 and 90 Pa·s, between 20 and 80 Pa·s, between 25 and 70 Pa·s, between 30 and 60 Pa·s, or the like.

The binder can comprise any biocompatible liquid material that can be mixed with a conductive element (preferably metallic crystals of silver or zinc) to create a conductive solution which can be applied to a substrate. One suitable binder is a solvent reducible polymer, such as the polyacrylic non-toxic silk-screen ink manufactured by COLORCON® Inc., a division of Berwind Pharmaceutical Services, Inc. (see COLORCON® NO-TOX® product line, part number NT28). In an embodiment the binder is mixed with high purity (at least 99.99%, in an embodiment) metallic silver crystals to make the silver conductive solution. The silver crystals, which can be made by grinding silver into a powder, are preferably smaller than 100 microns in size or about as fine as flour. In an embodiment, the size of the crystals is about 325 mesh, which is typically about 40 microns in size or a little smaller. The binder is separately mixed with high purity (at least 99.99%, in an embodiment) metallic zinc powder which has also preferably been sifted through standard 325 mesh screen, to make the zinc conductive solution.

Other powders of metal can be used to make other conductive metal solutions in the same way as described in other embodiments.

When COLORCON® polyacrylic ink is used as the binder, about 10 to 40 percent of the mixture should be metal for a long term bandage (for example, one that stays on for about 10 days). For example, for a long term LLEC or LLEF system the percent of the mixture that should be metal can be 8 percent, or 10 percent, 12 percent, 14 percent, 16 percent, 18 percent, 20 percent, 22 percent, 24 percent, 26 percent, 28 percent, 30 percent, 32 percent, 34 percent, 36 percent, 38 percent, 40 percent, 42 percent, 44 percent, 46 percent, 48 percent, 50 percent, or the like.

If the same binder is used, but the percentage of the mixture that is metal is increased to 60 percent or higher, a typical system will be effective for longer. For example, for a longer term device, the percent of the mixture that should be metal can be 40 percent, or 42 percent, 44 percent, 46 percent, 48 percent, 50 percent, 52 percent, 54 percent, 56 percent, 58 percent, 60 percent, 62 percent, 64 percent, 66 percent, 68 percent, 70 percent, 72 percent, 74 percent, 76 percent, 78 percent, 80 percent, 82 percent, 84 percent, 86 percent, 88 percent, 90 percent, or the like.

For systems comprising a pliable substrate it can be desired to decrease the percentage of metal down to 5 percent or less, or to use a binder that causes the crystals to be more deeply embedded, so that the primary surface will be antimicrobial for a very long period of time and will not wear prematurely. Other binders can dissolve or otherwise break down faster or slower than a polyacrylic ink, so adjustments can be made to achieve the desired rate of spontaneous reactions from the voltaic cells.

To maximize the number of voltaic cells, in various embodiments, a pattern of alternating silver masses (e.g., 6 as shown in FIG. 1) or electrodes or reservoirs and zinc masses (e.g., 10 as shown in FIG. 1) or electrodes or reservoirs can create an array of electrical currents across the substrate. A basic embodiment, shown in FIG. 1, has each mass of silver randomly spaced from masses of zinc, and has each mass of zinc randomly spaced from masses of silver, according to an embodiment. In another embodiment, mass of silver can be equally spaced from masses of zinc, and has each mass of zinc equally spaced from masses of silver. That is, the electrodes or reservoirs or dots can either be a uniform pattern, a random pattern, or a combination of the like. For an exemplary device comprising silver and zinc, each silver design preferably has about twice as much mass as each zinc design, in an embodiment. For the embodiment in FIG. 1, the silver designs are most preferably about a millimeter from each of the closest four zinc designs, and vice-versa. The resulting pattern of dissimilar metal masses defines an array of voltaic cells when introduced to an electrolytic solution.

Figure 5:
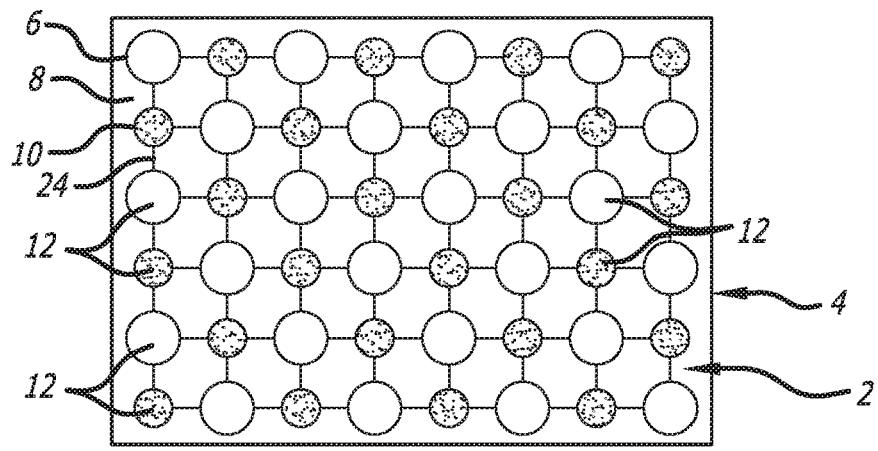
FIG. 5 depicts a detailed plan view of an alternate substrate embodiment disclosed herein which includes fine lines of conductive metal solution connecting electrodes.

FIG. 5 shows an additional feature that can initiate the flow of current in a poor electrolytic solution. A fine line 24 is printed using one of the conductive metal solutions along a current path of each voltaic cell. The fine line will initially have a direct reaction but will be depleted until the distance between the electrodes increases to where maximum voltage is realized. The initial current produced is intended to help control edema so that the system will be effective. If the electrolytic solution is highly conductive when the system is initially applied the fine line can be quickly depleted and the device will function as though the fine line had never existed.

Figure 6:
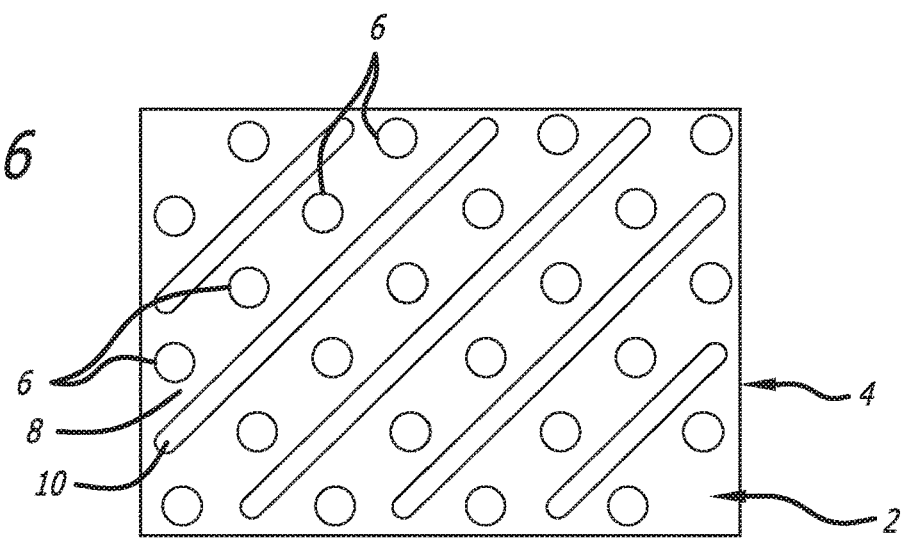
FIG. 6 depicts a detailed plan view of another alternate substrate embodiment having a line pattern and dot pattern.
Figure 7:
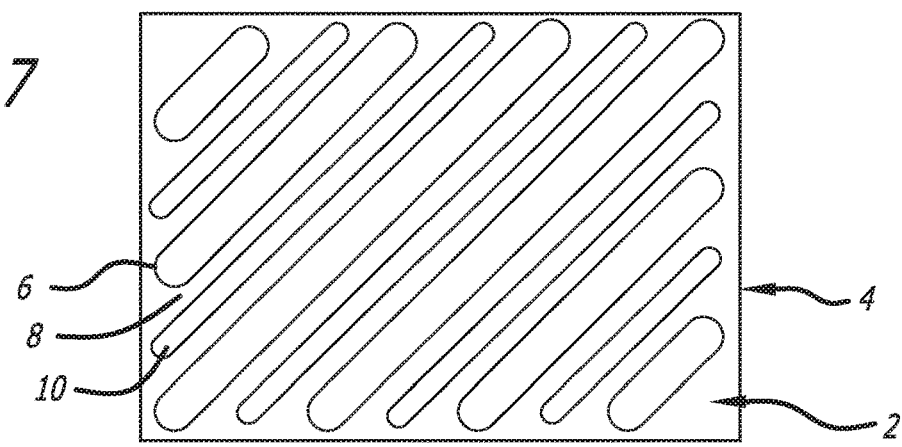
FIG. 7 depicts a detailed plan view of another alternate substrate embodiment having two line patterns.

FIGS. 6 and 7 show alternative patterns that use at least one line design. The first electrode 6 of FIG. 6 is a round dot similar to the first design used in FIG. 1. The second electrode 10 of FIG. 6 is a line. When the designs are repeated, they define a pattern of parallel lines that are separated by numerous spaced dots. FIG. 7 uses only line designs. The first electrode 6 can be thicker or wider than the second electrode 10 if the oxidation-reduction reaction requires more metal from the first conductive element (mixed into the first design's conductive metal solution) than the second conductive element (mixed into the second design's conductive metal solution). The lines can be dashed. Another pattern can be silver grid lines that have zinc masses in the center of each of the cells of the grid. The pattern can be letters printed from alternating conductive materials so that a message can be printed onto the primary surface-perhaps a brand name or identifying information such as patient blood type.

FIG. 8 shows an embodiment utilizing two electrodes (one positive and one negative). Upper arms 80 and 85 can be 1, 2, 3, or 4 mm in width. Lower arm 87 and serpentine 89 can be 1, 2, 3, or 4 mm in width. The electrodes can be 1, 2, or 3 mm in depth.

FIG. 9 shows an embodiment utilizing two electrodes (one positive and one negative). Upper arms 90 and 95 can be 1, 2, 3, or 4 mm in width. The extensions protruding from the lower arm 96 can be 1, 1.5, 2, 2.5, 3, 3.5, or 4 mm in width. The extensions protruding from the comb 98 can be 1, 2, 3, 4, 5, 6, or 7 mm in width. The electrodes can be 1, 2, or 3 mm in depth.

Figure 10:
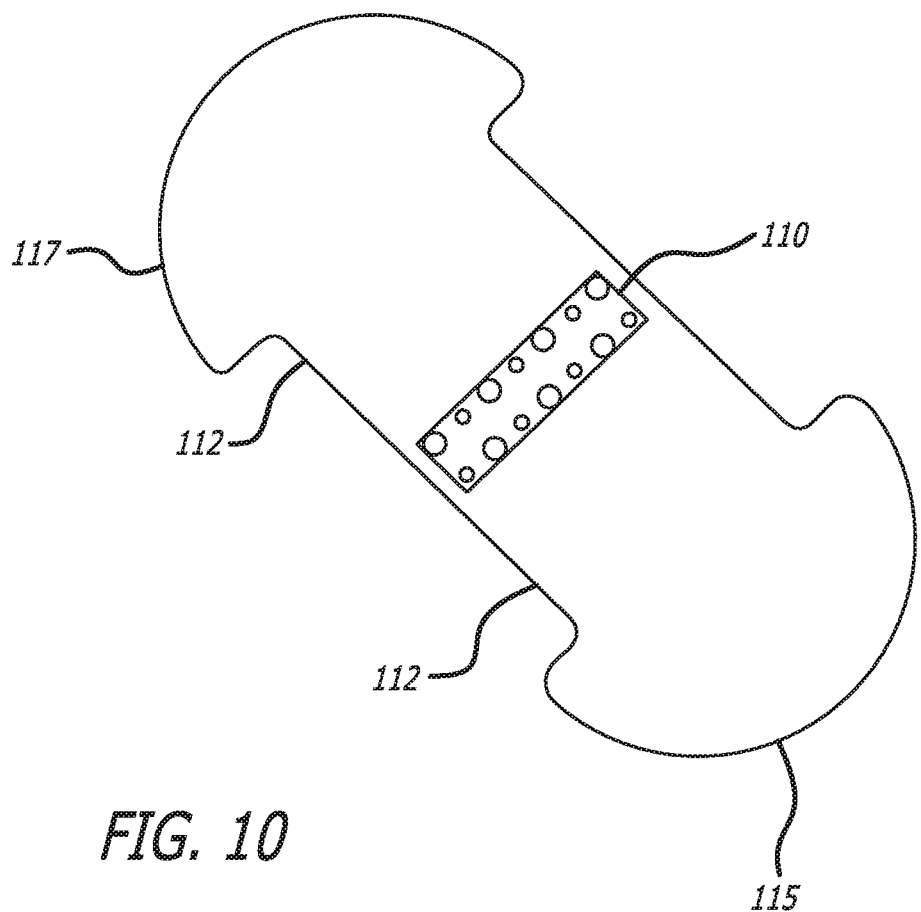
FIG. 10 an embodiment using the applied pattern of FIG. 1 according to one or more embodiments.

FIG. 10 shows an embodiment utilizing a multi-electrode array 110 of the pattern in FIG. 1. Elongated areas 115 and 117 aid in securing the dressing. As seen in the Figure, multi electrode array 110 can form a rectangular pattern with its long axis perpendicular to the long axis of the dressing. The substrate can extend beyond the array as seen in the Figure. The length of the dressing along its long axis can be, for example, 25, 30, 40, 50, 60, 70, 80, 90, 100, 120, 140, 160, 180, 200, 250, 300, 350, 400, 450 mm, or more. Elongated areas 115, 117 can be radiused to form a half-circle as shown in the Figure. The length of the dressing along its short axis can be, for example, 10, 12, 14, 16, 18, 20, 22, 24, 26, 28, 30, 32, 34, 36, 38, 40, 42, 44, 46, 48, 50, 52, or 54 mm, or more. Recessed area 112 can be present on either or both sides of the dressing. The dressing can comprise a port to allow for access to the interior of the dressing or, for example, the treatment area.

The width and depth of the various areas of the electrode can be designed to produce a particular electric field, or, when both electrodes are in contact with a conductive material, a particular electric current. For example, the width of the various areas of the electrode can be, for example, 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or 7 mm, or 8 mm, or 9 mm, or 10 mm, or 11 mm, or the like.

In embodiments, the depth or thickness of the various areas of the electrode can be, for example, 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or the like.

The shortest distance between the two electrodes in an embodiment can be, for example, 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, or the like.

In embodiments, the length of the long axis of the device can be, for example, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 75 mm, 100 mm, 150 mm, 200 mm, 250 mm, 300 mm, 350 mm, 400 mm, 450 mm, 500 mm, 600 mm, 700 mm, 800 mm, 900 mm, 1000 mm, or more, or the like.

In embodiments, the length of the short axis of the device can be, for example, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 75 mm, 100 mm, or more, or the like.

Because the spontaneous oxidation-reduction reaction of silver and zinc uses a ratio of approximately two silver to one zinc, the silver design can contain about twice as much mass as the zinc design in an embodiment. At a spacing of about 1 mm between the closest dissimilar metals (closest edge to closest edge) each voltaic cell that contacts a conductive fluid such as a cosmetic cream can create approximately 1 volt of potential that will penetrate substantially through its surrounding surfaces.

In certain embodiments the spacing between the closest conductive materials can be not more than 0.1 mm, not more than 0.2 mm, not more than 0.3 mm, not more than 0.4 mm, not more than 0.5 mm, not more than 0.6 mm, not more than 0.7 mm, not more than 0.8 mm, not more than 0.9 mm, not more than 1 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5 mm, not more than 5.1 mm, not more than 5.2 mm, not more than 5.3 mm, not more than 5.4 mm, not more than 5.5 mm, not more than 5.6 mm, not more than 5.7 mm, not more than 5.8 mm, not more than 5.9 mm, not more than 6 mm, or the like.

In certain embodiments spacing between the closest conductive materials can be not less than 0.1 mm, not less than 0.2 mm, not less than 0.3 mm, not less than 0.4 mm, not less than 0.5 mm, not less than 0.6 mm, not less than 0.7 mm, not less than 0.8 mm, not less than 0.9 mm, not less than 1 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5 mm, not less than 5.1 mm, not less than 5.2 mm, not less than 5.3 mm, not less than 5.4 mm, not less than 5.5 mm, not less than 5.6 mm, not less than 5.7 mm, not less than 5.8 mm, not less than 5.9 mm, not less than 6 mm, or the like.

Embodiments comprise systems and devices comprising a hydrophilic polymer base and a first electrode design formed from a first conductive liquid that comprises a mixture of a polymer and a first element, the first conductive liquid being applied into a position of contact with the primary surface, the first element comprising a metal species, and the first electrode design comprising at least one dot or reservoir, wherein selective ones of the at least one dot or reservoir have approximately a 1.5 mm +/−1 mm mean diameter; a second electrode design formed from a second conductive liquid that comprises a mixture of a polymer and a second element, the second element comprising a different metal species than the first element, the second conductive liquid being printed into a position of contact with the primary surface, and the second electrode design comprising at least one other dot or reservoir, wherein selective ones of the at least one other dot or reservoir have approximately a 2 mm +/−2 mm mean diameter; a spacing on the primary surface that is between the first electrode design and the second electrode design such that the first electrode design does not physically contact the second electrode design, wherein the spacing is approximately 1.5 mm +/−1 mm, and at least one repetition of the first electrode design and the second electrode design, the at least one repetition of the first electrode design being substantially adjacent the second electrode design, wherein the at least one repetition of the first electrode design and the second electrode design, in conjunction with the spacing between the first electrode design and the second electrode design, defines at least one pattern of at least one voltaic cell for spontaneously generating at least one electrical current when introduced to an electrolytic solution. Therefore, electrodes, dots or reservoirs can have a mean diameter or width of 0.2 mm, or 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, or the like.

The material concentrations or quantities within and/or the relative sizes (e.g., dimensions or surface area) of the first and second (or more) reservoirs or dots or electrodes can be selected specifically to control various characteristics of the systems' behavior. For example, the quantities of material within a first and second reservoir can be selected to provide an apparatus having an operational behavior that depletes at approximately a desired rate and/or that "dies" after an approximate period of time after activation. In an embodiment the one or more first reservoirs and the one or more second reservoirs are configured to sustain one or more currents for an approximate pre-determined period of time, after activation. It is to be understood that the amount of time that currents are sustained can depend on external conditions and factors (e.g., the quantity and type of activation material), and currents can occur intermittently depending on the presence or absence of activation material.

In various embodiments the difference of the standard potentials of the first and second reservoirs can be in a range from 0.05 V to approximately 5.0 V or more. For example, the standard potential can be 0.05 V, or 0.06 V, 0.07 V, 0.08 V, 0.09 V, 0.1 V, 0.2 V, 0.3 V, 0.4 V, 0.5 V, 0.6 V, 0.7 V, 0.8 V, 0.9 V, 1.0 V, 1.1 V, 1.2 V, 1.3 V, 1.4 V, 1.5 V, 1.6 V, 1.7 V, 1.8 V, 1.9 V, 2.0 V, 2.1 V, 2.2 V, 2.3 V, 2.4 V, 2.5 V, 2.6 V, 2.7 V, 2.8 V, 2.9 V, 3.0 V, 3.1 V, 3.2 V, 3.3 V, 3.4 V, 3.5 V, 3.6 V, 3.7 V, 3.8 V, 3.9 V, 4.0 V, 4.1 V, 4.2 V, 4.3 V, 4.4 V, 4.5 V, 4.6 V, 4.7 V, 4.8 V, 4.9 V, 5.0 V, 5.1 V, 5.2 V, 5.3 V, 5.4 V, 5.5 V, 3.6 V, 5.7 V, 5.8 V, 3.9 V, 6.0 V, 4.1 V, 6.2 V, 6.3 V, 6.4 V, 6.5 V, 6.6 V, 6.7 V, 6.8 V, 6.9 V, 7.0 V, or the like.

In a particular embodiment the difference of the standard potentials of the first and second reservoirs or electrodes can be at least 0.05 V, or at least 0.06 V, at least 0.07 V, at least 0.08 V, at least 0.09 V, at least 0.1 V, at least 0.2 V, at least 0.3 V, at least 0.4 V, at least 0.5 V, at least 0.6 V, at least 0.7 V, at least 0.8 V, at least 0.9 V, at least 1.0 V, at least 1.1 V, at least 1.2 V, at least 1.3 V, at least 1.4 V, at least 1.5 V, at least 1.6 V, at least 1.7 V, at least 1.8 V, at least 1.9 V, at least 2.0 V, at least 2.1 V, at least 2.2 V, at least 2.3 V, at least 2.4 V, at least 2.5 V, at least 2.6 V, at least 2.7 V, at least 2.8 V, at least 2.9 V, at least 3.0 V, at least 3.1 V, at least 3.2 V, at least 3.3 V, at least 3.4 V, at least 3.5 V, at least 3.6 V, at least 3.7 V, at least 3.8 V, at least 3.9 V, at least 4.0 V, at least 4.1 V, at least 4.2 V, at least 4.3 V, at least 4.4 V, at least 4.5 V, at least 4.6 V, at least 4.7 V, at least 4.8 V, at least 4.9 V, at least 5.0 V, at least 5.1 V, at least 3.2 V, at least 5.3 V, at least 5.4 V, at least 5.5 V, at least 5.6 V, at least 5.7 V, at least 5.8 V, at least 5.9 V, at least 6.0 V, at least 6.1 V, at least 6.2 V, at least 6.3 V, at least 6.4 V, at least 6.5 V, at least 6.6 V, at least 6.7 V, at least 6.8 V, at least 6.9 V, at least 7.0 V, or the like.

In a particular embodiment, the difference of the standard potentials of the first and second reservoirs or electrodes can be not more than 0.05 V, or not more than 0.06 V, not more than 0.07 V, not more than 0.08 V, not more than 0.09 V, not more than 0.1 V, not more than 0.2 V, not more than 0.3 V, not more than 0.4 V, not more than 0.5 V, not more than 0.6 V, not more than 0.7 V, not more than 0.8 V, not more than 0.9 V, not more than 1.0 V, not more than 1.1 V, not more than 1.2 V, not more than 1.3 V, not more than 1.4 V, not more than 1.5 V, not more than 1.6 V, not more than 1.7 V, not more than 1.8 V, not more than 1.9 V, not more than 2.0 V, not more than 2.1 V, not more than 2.2 V, not more than 2.3 V, not more than 2.4 V, not more than 2.5 V, not more than 2.6 V, not more than 2.7 V, not more than 2.8 V, not more than 2.9 V, not more than 3.0 V, not more than 3.1 V, not more than 3.2 V, not more than 3.3 V, not more than 3.4 V, not more than 3.5 V, not more than 3.6 V, not more than 3.7 V, not more than 3.8 V, not more than 3.9 V, not more than 4.0 V, not more than 4.1 V, not more than 4.2 V, not more than 4.3 V, not more than 4.4 V, not more than 4.5 V, not more than 4.6 V, not more than 4.7 V, not more than 4.8 V, not more than 4.9 V, not more than 5.0 V, or not more than 5.1 V, not more than 5.2 V, not more than 5.3 V, not more than 5.4 V, not more than 5.5 V, not more than 5.6 V, not more than 5.7 V, not more than 5.8 V, not more than 5.9 V, not more than 6.0 V, not more than 6.1 V, not more than 6.2 V, not more than 6.3 V, not more than 6.4 V, not more than 6.5 V, not more than 6.6 V, not more than 6.7 V, not more than 6.8 V, not more than 6.9 V, not more than 7.0 V, or the like. In embodiments that include very small reservoirs (e.g., on the nanometer scale), the difference of the standard potentials can be substantially less or more. The electrons that pass between the first reservoir and the second reservoir can be generated as a result of the difference of the standard potentials.

The voltage present at the site of use of the system is typically in the range of millivolts but disclosed embodiments can introduce a much higher voltage, for example near 1 volt when using the 1 mm spacing of dissimilar metals already described. In this way the current not only can drive silver and zinc into the treatment if desired for treatment, but the current can also provide a stimulatory current so that the entire surface area can be treated. The electric field can also have beneficial effects on cell migration, ATP production, and angiogenesis.

A system or device disclosed herein can comprise an adhesive layer. In embodiments the adhesive layer is located on the non-treatment (non-contact) side of the substrate layer. The adhesive layer can maintain the position of the device on or about the treatment area, for example the skin.

In embodiments, the adhesive layer can comprise, for example, a Hi-Tack elastic, a conformable tape provided and a white liner. In an embodiment, the adhesive layer can comprise 3M™ 9904 High Tack Elastic Nonwoven Fabric Medical Tape. In embodiments, the adhesive layer comprises a "cutout" to allow exudate or other fluid from a treatment area to pass from the substrate layer to the absorbent foam layer. In embodiments the adhesive layer can be hypoallergenic. In embodiments the adhesive layer can comprise an acrylate, silicone, hydrocolloid, or rubber adhesive. In embodiments the adhesive layer can have a tensile strength of, for example, about 1, 2, 3, or 4 lbs/in of width. In embodiments the adhesive layer is located on the non-treatment side of the substrate layer. The adhesive layer can maintain the position of the device on or about the treatment area, for example the skin. In embodiments, the adhesive layer comprises a "cutout" to allow exudate or other fluid from a treatment area to pass from the substrate layer to an absorbent layer, for example foam.

A system or device disclosed herein can comprise an absorbent layer. In embodiments the absorbent layer is located on the adhesive layer on the side opposite the substrate layer. In embodiments, the absorbent layer comprises water, saline, hydrogel or an active agent to maintain hydration in the substrate layer.

In embodiments the absorbent layer is located on the substrate layer. In embodiments, the absorbent comprises water, saline, or an active agent to maintain hydration in the substrate layer.

The absorbent foam layer can comprise, for example, a medical-grade foam. For example, in embodiments the foam is certified to comply with the ISO 10993 protocol. In an embodiment the foam layer can comprise 3M™ TEGADERM™.

Active agents suitable for use with disclosed embodiments can comprise, for example, antibiotics. For example, antibiotics suitable for use with disclosed embodiments can comprise, for example, DRGN-1, amoxicillin, doxycycline, ceftaroline, cephalexin, ciprofloxacin, clindamycin, dalbavancin, metronidazole, azithromycin, sulfamethoxazole/trimethoprim, combinations thereof, or the like. In embodiments, disclosed antibiotics can comprise:

Antibiotics that cover methicillin-resistant *Staphylococcus aureus* (MRSA):
 a. Ceftobiprole
 b. Ceftaroline
 c. Clindamycin d. Dalbavancin
e. Daptomycin
f. Fusidic acid
g. Linezolid
h. Mupirocin (topical)
i. Oritavancin
j. Tedizolid
k. Telavancin
l. Tigecycline
m. Vancomycin Antibiotics that cover *Pseudomonas aeruginosa*:
a. Aminoglycosides
b. Carbapenems
c. Ceftazidime (3rd generation)
d. Cefepime (4th generation)
e. Ceftobiprole (5th generation)
f. Fluoroquinolones
g. Piperacillin/tazobactam
h. Ticarcillin/clavulanic acid Antibiotics that cover vancomycin-resistant *Enterococcus* (VRE):
a. Linezolid
b. Streptogramins
c. Tigecycline
d. Daptomycin A system or device disclosed herein can comprise a stretchable film layer. In embodiments the film layer can be breathable and stretchable. In embodiments the film layer can comprise, a polymer, for example, polyurethane. The film layer encapsulates and seals the absorbent foam layer, providing room for the foam layer to expand as well as maintaining hydration in the foam layer and thus the substrate layer. In embodiments, the film layer can stretch or expand to allow for expansion of the foam layer.

Systems and devices disclosed herein can comprise complementary areas on, for example, their perimeter that compliment other areas on the perimeter such that the areas engage with other areas on the device or with other devices by the fitting together of projections and recesses.

Embodiments disclosed herein can comprise a cosmetic product. For example, embodiments can comprise a skin care cream wherein the skin care cream is located between the skin and the electrode surface. Embodiments disclosed herein can comprise a cosmetic procedure. For example, embodiments can be employed before, after, or during a cosmetic procedure, such as before, after, or during a dermal filler injection. Certain embodiments can comprise use of a device disclosed herein before, after, or during a BOTOX® injection. Certain embodiments can comprise use of a device disclosed herein before, after, or during a resurfacing procedure.

Embodiments disclosed herein can comprise active agents or cosmetic agents or drugs, for example applied prior to applying the dressing to the treatment area, or applied to the substrate. Suitable active agents con comprise, for example, hypoallergenic agents, drugs, biologics, stem cells, growth factors, skin substitutes, cosmetic products, combinations, or combinations thereof, or the like. Stem cells can include, for example, embryonic stem cells, bone-marrow stem cells, adipose stem cells, and the like.

A growth factor is a naturally-occurring substance capable of stimulating cellular growth, proliferation, healing, and cellular differentiation, often a protein or a steroid hormone. Growth factors are important for regulating a variety of cellular processes. Growth factors typically act as signaling molecules between cells. Examples are cytokines and hormones that bind to specific receptors on the surface of their target cells. They often promote cell differentiation and maturation, which varies between growth factors. For example, bone morphogenetic proteins stimulate bone cell differentiation, while fibroblast growth factors and vascular endothelial growth factors stimulate blood vessel differentiation.

Growth factors can include, for example, Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor 1 or 2(FGF-1 or -2), Fetal Bovine Somatotrophin (FBS), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Keratinocyte growth factor (KGF), Migration-stimulating factor (MSF), Myostatin (GDF-8), Nerve growth factor (NGF) and other neurotrophins, Platelet-derived growth factor (PDGF), Thrombopoietin (TPO), T-cell growth factor (TCGF), Transforming growth factor alpha (TGF-α), Transforming growth factor beta (TGF-β), Tumor necrosis factor-alpha (TNF-α), Vascular endothelial growth factor (VEGF), Wnt Signaling Pathway, Placental growth factor (PGF), IL-1, IL-2, IL-3, IL-4, IL-5, IL-6, IL-7, Renalase, or combinations thereof. Active agents can include alpha granules.

In embodiments the system can comprise a port to access the interior of the device, for example the interior of the absorbent foam layer, for example to add active agents, carriers, solvents, or some other material. Certain embodiments can comprise a "blister" top that can enclose a material such as an antibacterial. In embodiments the blister top can contain a material that is released into or on to the material when the blister is pressed, for example a liquid or cream. For example, embodiments disclosed herein can comprise a blister top containing an antibacterial or the like.

In embodiments the system comprises a component such as elastic or other such fabric to maintain or help maintain its position. In embodiments the system comprises components such as straps to maintain or help maintain its position. In certain embodiments the system or device comprises a strap on either end of the long axis, or a strap linking on end of the long axis to the other. In embodiments that straps can comprise Velcro or a similar fastening system. In embodiments the straps can comprise elastic materials. In further embodiments the strap can comprise a conductive material, for example a wire to electrically link the device with other components, such as monitoring equipment or a power source. In embodiments the device can be wirelessly linked to monitoring or data collection equipment, for example linked via Bluetooth to a cell phone or computer that collects data from the device. In certain embodiments the device can comprise data collection means, such as temperature, pH, pressure, or conductivity data collection means.

In embodiments the positioning component can comprise an elastic film with an elasticity similar to that of skin, or greater than that of skin, or less than that of skin. In embodiments, the system can comprise a laminate where layers of the laminate can be of varying elasticities. For example, an outer layer may be highly elastic and an inner layer in-elastic or less elastic. The in-elastic layer can be made to stretch by placing stress relieving discontinuous regions through the thickness of the material so there is a mechanical displacement rather than stress that would break the hydrogel before stretching would occur. In embodiments the stress relieving discontinuous regions can extend completely through a layer or the system or can be placed where expansion is required. In embodiments of the system the stress relieving discontinuous regions do not extend all the way through the system or a portion of the system such as the substrate. In embodiments the discontinuous regions can pass halfway through the long axis of the substrate.

Devices and systems disclosed herein can comprise "anchor" regions or "arms" or straps to affix the system securely. The anchor regions or arms can anchor the system. For example, a system can be secured to an area proximal to a joint or irregular skin surface, and anchor regions of the system can extend to areas of minimal stress or movement to securely affix the system. Further, the system can reduce stress on an area, for example by "countering" the physical stress caused by movement.

In embodiments the system or device can comprise additional materials to aid in treatment.

In embodiments, the system or device can comprise instructions or directions on how to place the system to maximize its performance. Embodiments comprise a kit comprising a system or device and directions for its use. For example, embodiments can include a treatment method or protocol, such as a dressing replacement schedule. Disclosed kits can comprise active agents, for example antibacterials, or the like.

In certain embodiments dissimilar metals can be used to create an electric field with a desired voltage within the device or system. In certain embodiments the pattern of reservoirs can control the watt density and shape of the electric field.

Certain embodiments can utilize a power source to create the electric current, such as a battery or a micro-battery. The power source can be any energy source capable of generating a current in the system and can comprise, for example, AC power, DC power, radio frequencies (RF) such as pulsed RF, induction, ultrasound, and the like.

Dissimilar metals used to make a system or device disclosed herein can be, for example, silver and zinc. In certain embodiments the electrodes are coupled with a non-conductive material to create a random dot pattern or a uniform dot pattern within a hydrogel, most preferably an array or multi-array of voltaic cells that do not spontaneously react until they contact an electrolytic solution. Sections of this description use the terms "coated," "plated," or "printed" with "ink," but it is to be understood that a dot in a hydrogel may also be a solid microsphere of conductive material. The use of any suitable means for applying a conductive material is contemplated. In embodiments "coated," "plated," or "printed" can comprise any material such as a solution suitable for forming an electrode on a surface of a microsphere such as a conductive material comprising a conductive metal solution.

In another embodiment, "coated," "plated," or "printed" can comprise electroplating microspheres. Electroplating is a process that uses electric current to reduce dissolved metal cations so that they form a coherent metal coating on an electrode. Electroplating can be used to change the surface properties of microspheres or to build up thickness of a microsphere. Building thickness by electroplating microspheres can allow the microspheres to be form with a specific conductive material and at a specific gravity determined by the user.

In embodiments, printing devices can be used to produce systems and devices as disclosed herein. For example, inkjet or "3D" printers can be used to produce embodiments. In certain embodiments the binders or inks used to produce iontophoresis systems disclosed herein can comprise, for example, poly cellulose inks, poly acrylic inks, poly urethane inks, silicone inks, and the like. In embodiments the type of ink used can determine the release rate of electrons from the reservoirs. In embodiments various materials can be added to the ink or binder such as, for example, conductive or resistive materials can be added to alter the shape or strength of the electric field. Other materials, such as silicon, can be added to enhance scar reduction. Such materials can also be added to the spaces between reservoirs.

In certain embodiments, the system or device can be shaped to fit a particular region of the body.

Embodiments disclosed herein can comprise interlocking areas on the perimeter of that complement other areas on the perimeter such that the areas engage with each other by the fitting together of projections or protrusions and recesses or intrusions. Such embodiments provide several advantages, for example additional securing force for the device, as well as allowing a user to custom-fit the device over a specific area. This allows the administration of a tailored electric field to a particular area, for example a uniform electric field or a field of varying strength. In embodiments, multiple port sites or scope sites can be accommodated. In embodiments, these multiple port or scope sites can be provided without device overlap, but still providing complete coverage of the area where treatment is desired. Multiple port sites can be useful in embodiments used with adjunctive wound therapies, for example Negative Pressure Wound Therapy (NPWT) or Topical Oxygen Therapy (TOT). The port or scope sites can also be useful for accessing an injury, for example for use in arthroscopic surgery. The port or scope sites can comprise, for example, a void region in the substrate, or "slits" defining a section of the substrate such that the substrate can be peeled back to access the tissue beneath.

Certain embodiments disclosed herein comprise a method of manufacturing a LLEC or LLEF system, the method comprising coupling a substrate with one or more biocompatible electrodes configured to generate at least one of a low level electric field or low level electric current. The substrate can be planar. In another embodiment, the method comprises joining a substrate with one or more biocompatible electrodes comprising a first bioelectric element comprising a first microparticle formed from a first conductive material, and a second bioelectric element comprising a second microparticle formed from a second conductive material. For example, the first microparticle formed from a first conductive material can be a reducing agent. The second microparticle formed from a second conductive material can be an oxidizing agent.

Embodiments disclosed herein comprise iontophoresis systems that can produce an electrical stimulus and/or can electromotivate, electroconduct, electroinduct, electrotransport, and/or electrophorese one or more therapeutic materials in areas of target tissue (e.g., iontophoresis), and/or can cause one or more biologic or other materials in proximity to, on or within target tissue to be rejuvenated.

In certain embodiments, for example treatment methods, it can be preferable to utilize AC or DC current. For example, embodiments disclosed herein can employ phased array, pulsed, square wave, sinusoidal, or other wave forms, combinations, or the like. Certain embodiments utilize a controller, for example to produce and control power production and/or distribution to the device.

While various embodiments have been shown and described, it will be realized that alterations and modifications can be made thereto without departing from the scope of the following claims. It is expected that other methods of applying the conductive material can be substituted as appropriate. Also, there are numerous shapes, sizes and patterns of voltaic cells that have not been described but it is expected that this disclosure will enable those skilled in the art to incorporate their own designs which will then which will become active when brought into contact with an electrolytic solution.

Methods of Use

Embodiments disclosed herein relating to treatment can also comprise selecting a patient or tissue in need of, or that could benefit by, using a disclosed system.

Methods disclosed herein can comprise applying a disclosed embodiment to an area to be treated. Embodiments can comprise selecting or identifying a patient in need of treatment, for example a patient who has received surgical treatment. In embodiments, methods disclosed herein can comprise formation and application of a system or device disclosed herein to an area to be treated.

Embodiments can comprise treatment or prevention of an infection, for example a deep tissue infection, or a biofilm, or the like.

Additional aspects include methods of preventing bacterial biofilm formation. Aspects also include a method of reducing microbial or bacterial proliferation, killing microbes or bacteria, killing bacteria through a biofilm layer, or preventing the formation of a biofilm. Embodiments include methods using devices disclosed herein in combination with antibiotics for reducing microbial or bacterial proliferation, killing microbes or bacteria, killing bacteria through a biofilm layer, or preventing the formation of a biofilm.

In embodiments, disclosed methods comprise application to the treatment area or the device of a system disclosed herein comprising an active agent.

In embodiments, disclosed methods include application to the treatment area or the device of an antibacterial. In embodiments the antibacterial can be, for example, alcohols, aldehydes, halogen-releasing compounds, peroxides, anilides, biguanides, bisphenols, halophenols, heavy metals, phenols and cresols, quaternary ammonium compounds, and the like. In embodiments the antibacterial agent can comprise, for example, ethanol, isopropanol, glutaraldehyde, formaldehyde, chlorine compounds, iodine compounds, hydrogen peroxide, ozone, peracetic acid, formaldehyde, ethylene oxide, triclocarban, chlorhexidine, alexidine, polymeric biguanides, triclosan, hexachlorophene, PCMX (p-chloro-m-xylenol), silver compounds, mercury compounds, phenol, cresol, cetrimide, benzalkonium chloride, cetylpyridinium chloride, ceftolozane/tazobactam, ceftazidime/avibactam, ceftaroline/avibactam, imipenem/MK-7655, plazomicin, eravacycline, brilacidin, and the like.

In embodiments, compounds that modify resistance to common antibacterials can be employed. For example, some resistance-modifying agents may inhibit multidrug resistance mechanisms, such as drug efflux from the cell, thus increasing the susceptibility of bacteria to an antibacterial. In embodiments, these compounds can include Phe—Arg-β-naphthylamide, or β-lactamase inhibitors such as clavulanic acid and sulbactam.

In embodiments the active agent can be, for example, positively or negatively charged. In embodiments, positively charged active agents can comprise centbucridine, tetracaine, Novocaine® (procaine), ambucaine, amolanone, amylcaine, benoxinate, betoxycaine, carticaine, chloroprocaine, cocaethylene, cyclomethycaine, butethamine, butoxycaine, carticaine, dibucaine, dimethisoquin, dimethocaine, diperodon, dyclonine, ecogonidine, ecognine, euprocin, fenalcomine, formocaine, hexylcaine, hydroxyteteracaine, leucinocaine, levoxadrol, metabutoxycaine, myrtecaine, butamben, bupivicaine, mepivacaine, beta-adrenoceptor antagonists, opioid analgesics, butanilicaine, ethyl aminobenzoate, fomocine, hydroxyprocaine, isobutyl p-aminobenzoate, naepaine, octacaine, orthocaine, oxethazaine, parenthoxycaine, phenacine, phenol, piperocaine, polidocanol, pramoxine, prilocalne, propanocaine, proparacaine, propipocaine, pseudococaine, pyrrocaine, salicyl alcohol, parethyoxycaine, piridocaine, risocaine, tolycaine, trimecaine, tetracaine, anticonvulsants, antihistamines, articaine, cocaine, procaine, amethocaine, chloroprocaine, marcaine, chloroprocaine, etidocaine, prilocaine, lignocaine, benzocaine, zolamine, ropivacaine, and dibucaine, dexamethasone phosphate, combinations thereof.

Embodiments disclosed herein can be used to treat irregular surfaces of the body, including the face, the shoulder, the elbow, the wrist, the finger joints, the hip, the knee, the ankle, the toe joints, etc. Additional embodiments disclosed herein can be used in areas where tissue is prone to movement, for example the eyelid, the ear, the lips, the nose, the shoulders, the back, etc.

EXAMPLES

The following non-limiting example is provided for illustrative purposes only in order to facilitate a more complete understanding of representative embodiments. This example should not be construed to limit any of the embodiments described in the present specification.

Example 1

Cell Migration Assay

The in vitro scratch assay is an easy, low-cost and well-developed method to measure cell migration in vitro. The basic steps involve creating a "scratch" in a cell monolayer, capturing images at the beginning and at regular intervals during cell migration to close the scratch, and comparing the images to quantify the migration rate of the cells. Compared to other methods, the in vitro scratch assay is particularly suitable for studies on the effects of cell—matrix and cell—cell interactions on cell migration, mimic cell migration during wound healing in vivo and are compatible with imaging of live cells during migration to monitor intracellular events if desired. In addition to monitoring migration of homogenous cell populations, this method has also been adopted to measure migration of individual cells in the leading edge of the scratch. Not taking into account the time for transfection of cells, in vitro scratch assay per se usually takes from several hours to overnight.

Human keratinocytes were plated under plated under placebo or a LLEC system (substrate layer as described herein; "PROCELLERA®"). Cells were also plated under silver-only or zinc-only dressings. After 24 hours, the scratch assay was performed. Cells plated under the PROCELLERA® device displayed increased migration into the "scratched" area as compared to any of the zinc, silver, or placebo dressings. After 9 hours, the cells plated under the PROCELLERA® device had almost "closed" the scratch. This demonstrates the importance of electrical activity to cell migration and infiltration.

In addition to the scratch test, genetic expression was tested. Increased insulin growth factor (IGF)-1R phosphorylation was demonstrated by the cells plated under the PROCELLERA® device as compared to cells plated under insulin growth factor alone.

Integrin accumulation also affects cell migration. An increase in integrin accumulation was achieved with the LLEC system. Integrin is necessary for cell migration, and is found on the leading edge of migrating cell.

Thus, the tested LLEC system enhanced cellular migration and IGF-1R/integrin involvement. This involvement demonstrates the effect that the LLEC system had upon cell receptors involved with the wound healing process.

Example 2

Zone of Inhibition Test

For cellular repair to be most efficient, available energy should not be shared with ubiquitous microbes. In this "zone of inhibition" test, placebo, a LLEC device (substrate layer as described herein; PROCELLERA®) and silver only were tested in an agar medium with a 24 hour growth of organisms. Bacteria grew over the placebo, there was a zone of inhibition over the PROCELLERA® and a minimal inhibition zone over the silver. Because the samples were "buried" in agar, the electricidal effect of the LLEC system could be tested. This could mean the microbes were affected by the electrical field or the silver ion transport through the agar was enhanced in the presence of the electric field. Silver ion diffusion, the method used by silver based antimicrobials, alone was not sufficient. The test demonstrates the improved bactericidal effect of PROCELLERA® as compared to silver alone.

Example 3

Wound Care Study

The medical histories of patients who received "standard-of-care" wound treatment ("SOC"; n=20), or treatment with a LLEC substrate as disclosed herein (n=18), were reviewed. The wound care device used in the present study consisted of a discrete matrix of silver and zinc dots. A sustained voltage of approximately 0.8 V was generated between the dots. The electric field generated at the device surface was measured to be 0.2-1.0 V, 10-50 µA.

Wounds were assessed until closed or healed. The number of days to wound closure and the rate of wound volume reduction were compared. Patients treated with LLEC substrate received one application of the device each week, or more frequently in the presence of excessive wound exudate, in conjunction with appropriate wound care management. The LLEC substrate was kept moist by saturating with normal saline or conductive hydrogel. Adjunctive therapies (such as negative pressure wound therapy [NPWT], etc.) were administered with SOC or with the use of the LLEC substrate unless contraindicated. The SOC group received the standard of care appropriate to the wound, for example antimicrobial dressings, barrier creams, alginates, silver dressings, absorptive foam dressings, hydrogel, enzymatic debridement ointment, NPWT, etc. Etiology-specific care was administered on a case-by-case basis. Dressings were applied at weekly intervals or more. The SOC and LLEC groups did not differ significantly in gender, age, wound types or the length, width, and area of their wounds.

Wound dimensions were recorded at the beginning of the treatment, as well as interim and final patient visits. Wound dimensions, including length (L), width (W) and depth (D) were measured, with depth measured at the deepest point. Wound closure progression was also documented through digital photography. Determining the area of the wound was performed using the length and width measurements of the wound surface area.

Closure was defined as 100% epithelialization with visible effacement of the wound. Wounds were assessed 1 week post-closure to ensure continued progress toward healing during its maturation and remodeling phase.

Wound types included in this study were diverse in etiology and dimensions, thus the time to heal for wounds was distributed over a wide range (9-124 days for SOC, and 3-44 days for the LLEC group). Additionally, the patients often had multiple co-morbidities, including diabetes, renal disease, and hypertension. The average number of days to wound closure was 36.25 (SD=28.89) for the SOC group and 19.78 (SD=14.45) for the LLEC group, p=0.036. On average, the wounds in the LLEC treatment group attained closure 45.43% earlier than those in the SOC group.

Based on the volume calculated, some wounds improved persistently while others first increased in size before improving. The SOC and the LLEC groups were compared to each other in terms of the number of instances when the dimensions of the patient wounds increased (i.e., wound treatment outcome degraded). In the SOC group, 10 wounds (50% for n=20) became larger during at least one measurement interval, whereas 3 wounds (16.7% for n=18) became larger in the LLEC group (p=0.018). Overall, wounds in both groups responded positively. Response to treatment was observed to be slower during the initial phase, but was observed to improve as time progressed.

The LLEC wound treatment group demonstrated on average a 45.4% faster closure rate as compared to the SOC group. Wounds receiving SOC were more likely to follow a "waxing-and-waning" progression in wound closure compared to wounds in the LLEC treatment group.

Compared to localized SOC treatments for wounds, the LLEC (1) reduces wound closure time, (2) has a steeper wound closure trajectory, and (3) has a more robust wound healing trend with fewer incidence of increased wound dimensions during the course of healing.

Example 4

LLEC Influence on Human Keratinocyte Migration

An LLEC-generated electrical field was mapped, leading to the observation that LLEC generates hydrogen peroxide, known to drive redox signaling. LLEC-induced phosphorylation of redox-sensitive IGF-1R was directly implicated in cell migration. The LLEC also increased keratinocyte mitochondrial membrane potential.

The LLEC substrate was made of polyester printed with dissimilar elemental metals. It comprises alternating circular regions of silver and zinc dots, along with a proprietary, biocompatible binder added to lock the electrodes to the surface of a flexible substrate in a pattern of discrete reservoirs. When the LLEC contacts an aqueous solution, the silver positive electrode (cathode) is reduced while the zinc negative electrode (anode) is oxidized. The LLEC used herein consisted of metals placed in proximity of about 1 mm to each other thus forming a redox couple and generating an ideal potential on the order of 1 Volt. The calculated values of the electric field from the LLEC were consistent with the magnitudes that are typically applied (1-10 V/cm)

in classical electrotaxis experiments, suggesting that cell migration observed with the bioelectric dressing is likely due to electrotaxis.

Measurement of the potential difference between adjacent zinc and silver dots when the LLEC is in contact with de-ionized water yielded a value of about 0.2 Volts. Though the potential difference between zinc and silver dots can be measured, non-intrusive measurement of the electric field arising from contact between the LLEC and liquid medium was difficult. Keratinocyte migration was accelerated by exposure to an Ag/Zn LLEC. Replacing the Ag/Zn redox couple with Ag or Zn alone did not reproduce the effect of keratinocyte acceleration.

Exposing keratinocytes to an LLEC for 24 h significantly increased green fluorescence in the dichlorofluorescein (DCF) assay indicating generation of reactive oxygen species under the effect of the LLEC. To determine whether $H_2O_2$ is generated specifically, keratinocytes were cultured with a LLEC or placebo for 24 h and then loaded with PF6-AM (Peroxyfluor-6 acetoxymethyl ester; an indicator of endogenous $H_2O_2$). Greater intracellular fluorescence was observed in the LLEC keratinocytes compared to the cells grown with placebo. Over-expression of catalase (an enzyme that breaks down $H_2O_2$) attenuated the increased migration triggered by the LLEC. Treating keratinocytes with N-Acetyl Cysteine (which blocks oxidant-induced signaling) also failed to reproduce the increased migration observed with LLEC. Thus, $H_2O_2$ signaling mediated the increase of keratinocyte migration under the effect of the electrical stimulus.

External electrical stimulus can up-regulate the TCA (tricarboxylic acid) cycle. The stimulated TCA cycle is then expected to generate more NADH and $FADH_2$ to enter into the electron transport chain and elevate the mitochondrial membrane potential ($\Delta m$). Fluorescent dyes JC-1 and TMRM were used to measure mitochondrial membrane potential. JC-1 is a lipophilic dye which produces a red fluorescence with high $\Delta m$ and green fluorescence when $\Delta m$ is low. TMRM produces a red fluorescence proportional to $\Delta m$. Treatment of keratinocytes with LLEC for 24 h demonstrated significantly high red fluorescence with both JC-1 and TMRM, indicating an increase in mitochondrial membrane potential and energized mitochondria under the effect of the LLEC. As a potential consequence of a stimulated TCA cycle, available pyruvate (the primary substrate for the TCA cycle) is depleted resulting in an enhanced rate of glycolysis. This can lead to an increase in glucose uptake in order to push the glycolytic pathway forward. The rate of glucose uptake in HaCaT cells treated with LLEC was examined next. More than two fold enhancement of basal glucose uptake was observed after treatment with LLEC for 24 h as compared to placebo control.

Keratinocyte migration is known to involve phosphorylation of a number of receptor tyrosine kinases (RTKs). To determine which RTKs are activated as a result of LLEC, scratch assay was performed on keratinocytes treated with LLEC or placebo for 24 h. Samples were collected after 3 h and an antibody array that allows simultaneous assessment of the phosphorylation status of 42 RTKs was used to quantify RTK phosphorylation. It was determined that LLEC significantly induces IGF-1R phosphorylation. Sandwich ELISA using an antibody against phospho-IGF-1R and total IGF-1R verified this determination. As observed with the RTK array screening, potent induction in phosphorylation of IGF-1R was observed 3 h post scratch under the influence of LLEC. IGF-1R inhibitor attenuated the increased keratinocyte migration observed with LLEC treatment.

MBB (monobromobimane) alkylates thiol groups, displacing the bromine and adding a fluorescent tag (lamda emission=478 nm). MCB (monochlorobimane) reacts with only low molecular weight thiols such as glutathione. Fluorescence emission from UV laser-excited keratinocytes loaded with either MBB or MCB was determined for 30 min. Mean fluorescence collected from 10,000 cells showed a significant shift of MBB fluorescence emission from cells. No significant change in MCB fluorescence was observed, indicating a change in total protein thiol but not glutathione. HaCaT cells were treated with LLEC for 24 h followed by a scratch assay. Integrin expression was observed by immuno-cytochemistry at different time points. Higher integrin expression was observed 6 h post scratch at the migrating edge.

Consistent with evidence that cell migration requires $H_2O_2$ sensing, we determined that by blocking $H_2O_2$ signaling by decomposition of $H_2O_2$ by catalase or ROS scavenger, N-acetyl cysteine, the increase in LLEC-driven cell migration is prevented. The observation that the LLEC increases $H_2O_2$ production is significant because in addition to cell migration, hydrogen peroxide generated in the wound margin tissue is required to recruit neutrophils and other leukocytes to the wound, regulates monocyte function, and VEGF signaling pathway and tissue vascularization. Therefore, external electrical stimulation can be used as an effective strategy to deliver low levels of hydrogen peroxide over time to mimic the environment of the healing wound and thus should help improve wound outcomes. Another phenomenon observed during re-epithelialization is increased expression of the integrin subunit $\alpha v$. There is evidence that integrin, a major extracellular matrix receptor, polarizes in response to applied ES and thus controls directional cell migration. It may be noted that there are a number of integrin subunits, however we chose integrin $\alpha v$ because of evidence of association of $\alpha v$ integrin with IGF-1R, modulation of IGF-1 receptor signaling, and of driving keratinocyte locomotion. Additionally, integrin$_{\alpha v}$ has been reported to contain vicinal thiols that provide site for redox activation of function of these integrins and therefore the increase in protein thiols that we observe under the effect of ES may be the driving force behind increased integrin mediated cell migration. Other possible integrins which may be playing a role in LLEC-induced IGF-1R mediated keratinocyte migration are $\alpha 5$ integrin and $\alpha 6$ integrin.

Materials and Methods

Cell culture—Immortalized HaCaT human keratinocytes were grown in Dulbecco's low-glucose modified Eagle's medium (Life Technologies, Gaithersburg, Md., U.S.A.) supplemented with 10% fetal bovine serum, 100 U/ml penicillin, and 100 μg/ml streptomycin. The cells were maintained in a standard culture incubator with humidified air containing 5% $CO_2$ at 37° C.

Scratch assay—A cell migration assay was performed using culture inserts (IBIDI®, Verona, Wis.) according to the manufacturers instructions. Cell migration was measured using time-lapse phase-contrast microscopy following withdrawal of the insert. Images were analyzed using the Axio-Vision Rel 4.8 software.

N-Acetyl Cysteine Treatment—Cells were pretreated with 5 mM of the thiol antioxidant N-acetylcysteine (Sigma) for 1 h before start of the scratch assay.

IGF-1R inhibition—When applicable, cells were preincubated with 50 nM IGF-1R inhibitor, picropodophyllin (Calbiochem, Mass.) just prior to the Scratch Assay.

Cellular $H_2O_2$ Analysis—To determine intracellular $H_2O_2$ levels, HaCaT cells were incubated with 5 pM PF6-AM in PBS for 20 min at room temperature. After loading, cells were washed twice to remove excess dye and visualized using a Zeiss Axiovert 200M microscope.

Catalase gene delivery—HaCaT cells were transfected with $2.3 \times 10^7$ pfu AdCatalase or with the empty vector as control in 750 μL of media. Subsequently, 750 μL of additional media was added 4 h later and the cells were incubated for 72 h.

RTK Phosphorylation Assay—Human Phospho-Receptor Tyrosine Kinase phosphorylation was measured using Phospho-RTK Array kit (R & D Systems).

ELISA—Phosphorylated and total IGF-1R were measured using a DuoSet IC ELISA kit from R&D Systems.

Determination of Mitochondrial Membrane Potential—Mitochondrial membrane potential was measured in HaCaT cells exposed to the LLEC or placebo using TMRM or JC-1 (MitoProbe JC-1 Assay Kit for Flow Cytometry, Life Technologies), per manufacturers instructions for flow cytometry.

Integrin αV Expression—Human HaCaT cells were grown under the MCD or placebo and harvested 6 h after removing the IBIDI® insert. Staining was done using antibody against integrin αV (Abcam, Cambridge, Mass.).

Example 5

Generation of Superoxide

A LLEC substrate was tested to determine the effects on superoxide levels which can activate signal pathways. PROCELLERA® LLEC substrate increased cellular protein sulfhydryl levels. Further, the PROCELLERA® substrate increased cellular glucose uptake in human keratinocytes. Increased glucose uptake can result in greater mitochondrial activity and thus increased glucose utilization, providing more energy for cellular migration and proliferation. This can speed wound healing.

Example 6

Treatment of Surgical Site

A 29 year-old undergoes an appendectomy. Following the procedure, the doctor applies to the surgical site an embodiment as disclosed herein in FIG. 8. The device prevents post-surgical infection and stimulates healing.

Example 7

Treatment of Surgical Site

A 44 year-old undergoes a lower leg amputation. Following the procedure, the doctor applies to the surgical site an embodiment as disclosed herein in FIG. 9. The device prevents post-surgical infection (including biofilm formation) and stimulates healing.

Example 8

Treatment of Diabetic Ulcer

A 59 year-old has diabetic ulcers on his lower legs. The ulcers have proved resistant to conventional treatments. The patient's doctor applies deep-tissue treatment dressings as described herein to the ulcers to prevent infection and stimulate healing.

Example 9

Treatment Following Knee Replacement

A 84 year-old male undergoes knee replacement surgery. Following the procedure, the doctor applies a deep treatment wound dressing designed for the knee as described herein. The dressing stimulates healing and prevents post-surgical infection while providing full articulation of the joint and avoiding excess shear force on the surrounding skin.

Example 10

Treatment Following Hip Replacement

A 84 year-old male undergoes hip replacement surgery. Following the procedure, the doctor applies a deep treatment composite wound dressing designed for the hip as described herein. The dressing stimulates healing and prevents post-surgical infection while providing full articulation of the joint and avoiding excess shear force on the surrounding skin. The dressing can expand as it absorbs wound exudate without increasing shear force on the surrounding skin.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, comprising the best mode known to the inventor for carrying out the methods and devices described herein. Of course, variations on these described embodiments will become apparent to those of ordinary skill in the art upon reading the foregoing description. Accordingly, this disclosure comprises all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be comprised in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A deep tissue treatment device comprising a substrate layer comprising a pliable material comprising two biocompatible electrodes configured to generate a uniform low level electric field (LLEF) to a depth of at least 10 mm, wherein at least one of said electrodes comprises a serpentine region, wherein the first electrode is formed from a first conductive material, and the second electrode is formed from a second conductive material, and wherein the two biocompatible electrodes spontaneously generate the LLEF.

2. The device of claim 1, wherein the first electrode and the second electrode spontaneously generate a LLEC when contacted with an electrolytic solution or with a conductive fluid.

3. The device of claim 1, wherein the LLEF is at least 1.0 Volt.

4. The device of claim 3, wherein the LLEF is at least 3.0 Volts.

5. The device of claim 3, wherein the LLEF is at least 6.0 Volts.

6. The device of claim 2, wherein the LLEC is between 400 and 450 micro-amperes.

7. The device of claim 2, wherein the LLEC is between 450 and 500 micro-amperes.

8. The device of claim 2, wherein the LLEC is between 500 and 550 micro-amperes.

9. The device of claim 1, further comprising an expandable absorbent layer, wherein the expandable absorbent layer can, upon exposure to a liquid, expand away from a treatment area.

* * * * *